(12) United States Patent
Utsunomiya et al.

(10) Patent No.: US 10,170,155 B2
(45) Date of Patent: Jan. 1, 2019

(54) MOTION INFORMATION DISPLAY APPARATUS AND METHOD

(71) Applicant: TOSHIBA MEDICAL SYSTEMS CORPORATION, Otawara-Shi (JP)

(72) Inventors: Kazuki Utsunomiya, Nasushiobara (JP); Kousuke Sakaue, Nasushiobara (JP); Satoshi Ikeda, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/803,180

(22) Filed: Jul. 20, 2015

(65) Prior Publication Data

US 2015/0325270 A1 Nov. 12, 2015

Related U.S. Application Data

(63) Continuation of application No. PCT/JP2014/051140, filed on Jan. 21, 2014.

(30) Foreign Application Priority Data

Jan. 21, 2013 (JP) .................................. 2013-008605

(51) Int. Cl.
*G11B 27/30* (2006.01)
*G06K 9/00* (2006.01)
(Continued)

(52) U.S. Cl.
CPC ........ *G11B 27/3081* (2013.01); *A61B 5/1128* (2013.01); *G06F 19/00* (2013.01);
(Continued)

(58) Field of Classification Search
CPC .......................... G06K 9/00348; G11B 27/3081
(Continued)

(56) References Cited

U.S. PATENT DOCUMENTS

2006/0280333 A1 12/2006 Ikeda et al.
2007/0270214 A1* 11/2007 Bentley ................ A61B 5/1122
463/30
(Continued)

FOREIGN PATENT DOCUMENTS

JP 08-215177 A 8/1996
JP 09-56697 A 3/1997
(Continued)

OTHER PUBLICATIONS

International Search Report dated Mar. 11, 2014 for PCT/JP2014/051140 filed on Jan. 21, 2014 with English Translation.
(Continued)

*Primary Examiner* — Thai Q Tran
*Assistant Examiner* — Girumsew Wendmagegn
(74) *Attorney, Agent, or Firm* — Oblon, McClelland, Maier & Neustadt, L.L.P.

(57) ABSTRACT

A motion information display apparatus according to an embodiment includes obtaining circuitry, identifying circuitry, and display controlling circuitry. The obtaining circuitry obtains a plurality of pieces of moving image information, and motion information that indicates a motion of a subject included in each of the moving image information. The identifying circuitry identifies a frame corresponding to a timing of a predetermined motion, from each frame group included in each of the moving image information, based on the motion information. The display controlling circuitry performs display control of the plurality of pieces of moving image information, using the frame corresponding to a timing of a predetermined motion.

9 Claims, 18 Drawing Sheets

(51) Int. Cl.
*G06F 19/00* (2018.01)
*A61B 5/11* (2006.01)
*A61B 5/055* (2006.01)

(52) U.S. Cl.
CPC ..... *G06F 19/3481* (2013.01); *G06K 9/00342* (2013.01); *G06K 9/00348* (2013.01); *G06K 9/00355* (2013.01); *A61B 5/055* (2013.01)

(58) Field of Classification Search
USPC ........................................................ 386/230
See application file for complete search history.

(56) References Cited

U.S. PATENT DOCUMENTS

2009/0324191 A1* 12/2009 Reusens .................. G06T 15/50
386/353
2010/0280418 A1* 11/2010 Klose .................... A61B 5/1114
600/595
2012/0190505 A1* 7/2012 Shavit ................ A63B 71/0622
482/8
2013/0171601 A1* 7/2013 Yuasa .................... A61B 5/1114
434/258

FOREIGN PATENT DOCUMENTS

| | | | |
|---|---|---|---|
| JP | 2000-138927 A | | 5/2000 |
| JP | 2000138927 A | * 5/2000 | ............... A61B 5/11 |
| JP | 2006-350578 A | | 12/2006 |
| WO | WO 2012/039467 A1 | | 3/2012 |

OTHER PUBLICATIONS

Written Opinion dated Mar. 11, 2014 for PCT/JP2014/051140 filed on Jan. 21, 2014.

* cited by examiner

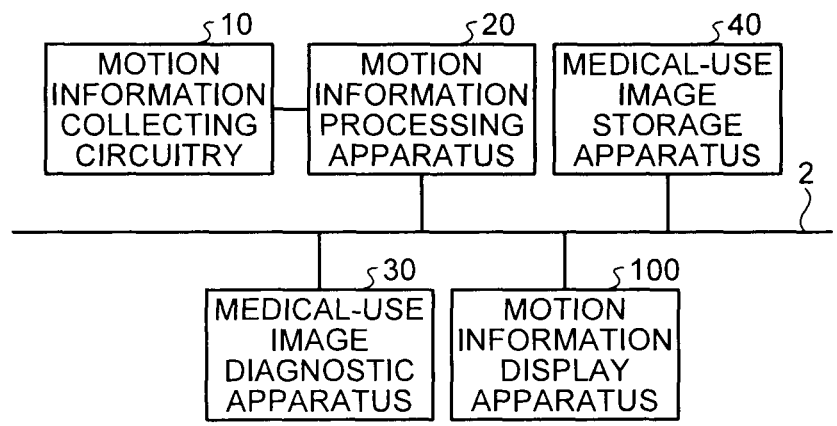
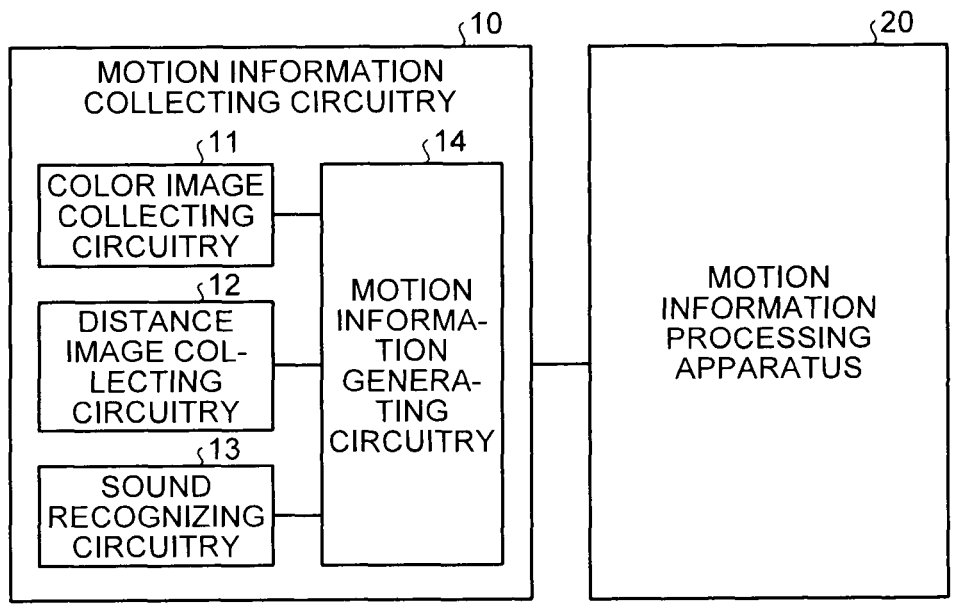

FIG.4

| JOINT RECOGNITION INFORMATION | COORDINATE INFORMATION |
|---|---|
| 3a | (x1, y1, z1) |
| 3b | (x2, y2, z2) |
| 3c | (x3, y3, z3) |
| 3d | (x4, y4, z4) |
| 3e | (x5, y5, z5) |
| 3f | (x6, y6, z6) |
| 3g | (x7, y7, z7) |
| 3h | (x8, y8, z8) |
| 3i | (x9, y9, z9) |
| 3j | (x10, y10, z10) |
| 3k | (x11, y11, z11) |
| 3l | (x12, y12, z12) |
| 3m | (x13, y13, z13) |
| 3n | (x14, y14, z14) |
| 3o | (x15, y15, z15) |
| 3p | (x16, y16, z16) |
| 3q | (x17, y17, z17) |
| 3r | (x18, y18, z18) |
| 3s | (x19, y19, z19) |
| 3t | (x20, y20, z20) |

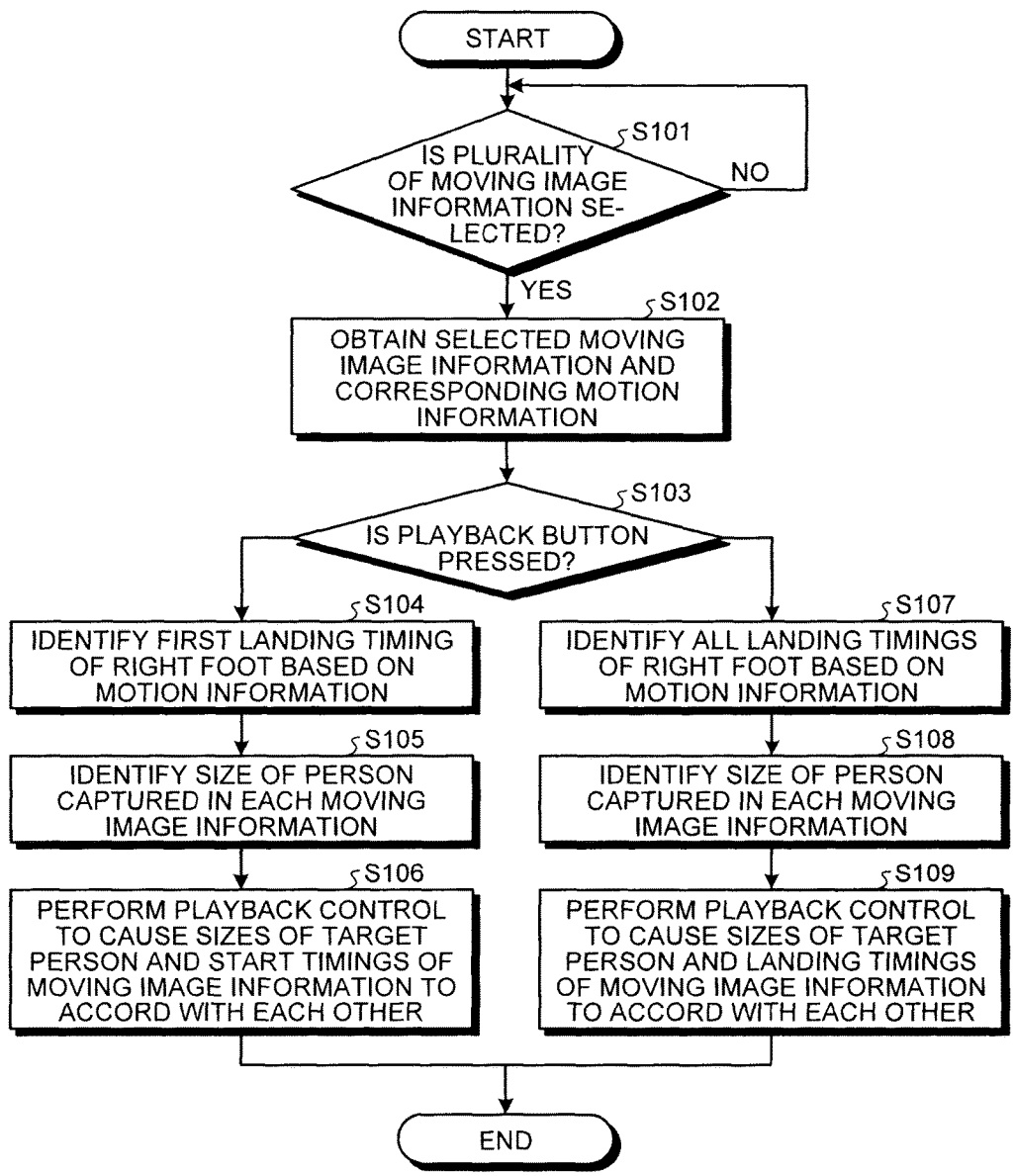

MOTION INFORMATION DISPLAY APPARATUS AND METHOD

CROSS-REFERENCE TO RELATED APPLICATIONS

This application is a continuation of PCT international application Ser. No. PCT/JP2014/051140 filed on Jan. 21, 2014 which designates the United States, incorporated herein by reference, and which claims the benefit of priority from Japanese Patent Application No. 2013-008605, filed on Jan. 21, 2013, the entire contents of which are incorporated herein by reference.

FIELD

Embodiments described herein relate generally to a motion information display apparatus and a method.

BACKGROUND

Conventionally, cooperative assistance by many specialists is performed in rehabilitation for the purpose of making a person's life better, the person being with mental and physical disabilities or a congenital disorder due to various causes such as a disease, an injury, or an aging process. For example, in the rehabilitation, cooperative assistance is performed by many specialists including a rehabilitation medical specialist, a rehabilitation nurse, a physical therapist, an occupational therapist, a speech-language-hearing therapist, a clinical psychologist, a prosthetist, and a social worker.

Meanwhile, in recent years, motion capture technologies that digitally record a movement of a person or an object have been developed. As systems of the motion capture technologies, an optical system, a mechanical system, a magnetic system, and a camera system are known. As an example, a camera system is known, which digitally record a movement of a person by causing the person to wear markers, detecting the markers with a tracker such as a camera, and processing the detected markers. Further, as a system without using the markers and the tracker, a system using an infrared light sensor is known, which digitally records a movement of a person by measuring a distance from the sensor to the person, and detecting various movements of the size or a skeleton of the person. As the sensor using such a system, Kinect (registered trademark) is known, for example.

BRIEF DESCRIPTION OF THE DRAWINGS

FIG. 1 is a block diagram illustrating a configuration diagram of a medical-use information system according to a first embodiment;

FIG. 2 is a block diagram illustrating a detailed configuration example of motion information collecting circuitry according to the first embodiment;

FIG. 4 is a diagram illustrating an example of skeleton information generated by the motion information generating circuitry according to the first embodiment;

FIG. 8 is a flowchart for describing an example of a processing procedure of the motion information display apparatus according to the first embodiment;

DETAILED DESCRIPTION

Figure 3A:
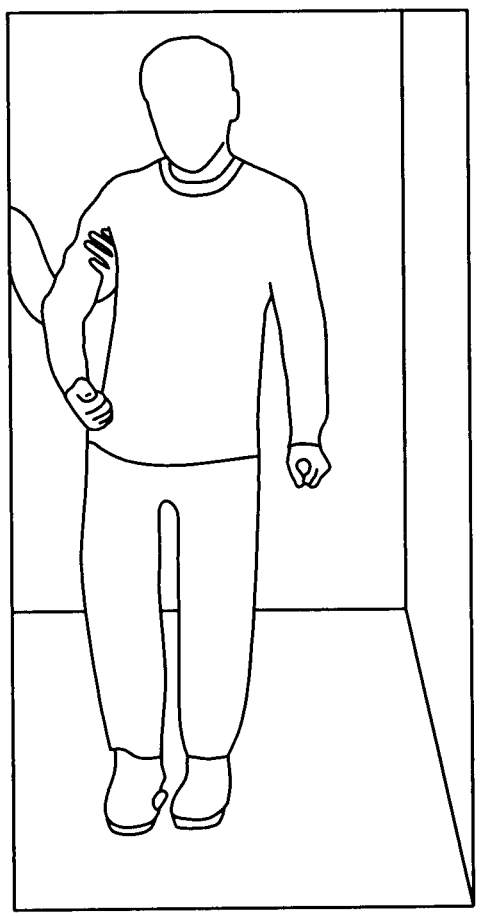
FIG. 3A is a diagram for describing processing of motion information generating circuitry according to the first embodiment.

A motion information display apparatus according to an embodiment includes obtaining circuitry, identifying circuitry, and display controlling circuitry. The obtaining circuitry obtains a plurality of pieces of moving image information, and motion information that indicates a motion of a subject included in each of the moving image information. The identifying circuitry identifies a frame corresponding to a timing of a predetermined motion, from each frame group included in each of the moving image information, based on the motion information. The display controlling circuitry performs display control of the plurality of pieces of moving image information, using the frame corresponding to a timing of a predetermined motion.

Hereinafter, a motion information display apparatus and a program according to embodiments will be described with reference to the drawings. Note that, the motion information display apparatus described below may be used as a single body of a motion information display apparatus, or may be used being incorporated in a system such as a medical record system or a rehabilitation department system, for example.

First Embodiment

FIG. 1 is a block diagram illustrating a configuration example of a medical-use information system according to a first embodiment. A medical-use information system 1 according to the first embodiment is a system that assists rehabilitation performed in a medical institution, a home, an office, and the like. Here, "rehabilitation" refers to a technique or a method for enhancing potential of a patient with a disorder, a chronic disease, or a disease of old age, which requires long lasting treatment, to recover and facilitate a life function and a social function. An example of the technique or the method includes function training for recovering and facilitating the life function and the social function. Here, examples of the function training include walking training and training of joint movable range. A person to be rehabilitated is written as "target person". The target person is, for example, a sick person, an injured person, an aged person, or a disabled person. Further, a person who assists the target person when rehabilitation is performed is written as "helper". The helper is, for example, a medical professional such as a doctor, a physical therapist or a nurse who engages in a medical institution, or a caregiver, a family member, or a friend who cares for the target person at home. Further, the rehabilitation is abbreviated as "rehab".

As illustrated in FIG. 1, the medical-use information system 1 according to the first embodiment includes motion information collecting circuitry 10, a motion information processing apparatus 20, a medical-use image diagnostic apparatus 30, a medical-use image storage apparatus 40, and a motion information display apparatus 100. The motion information processing apparatus 20, the medical-use image diagnostic apparatus 30, the medical-use image storage apparatus 40, and the motion information display apparatus 100 are in a state of being able to directly or indirectly communicate with each other by an in-hospital LAN (local area network) 2 installed in a hospital, for example. When a picture archiving and communication system (PACS) is introduced in the medical-use information system 1, for example, the devices mutually transmit/receive medical-use image information and the like according to a digital imaging and communications in medicine (DICOM) standard. Note that the motion information display apparatus 100 may also be called medical-use image display apparatus.

The motion information collecting circuitry 10 detects a motion of a person, an object, or the like in a space where rehabilitation is performed, and collects motion information that indicates the motion of a person, an object, or the like, and moving image information of the captured person or object. Note that, as the motion information collecting circuitry 10, Kinect (registered trademark) is used, for example.

FIG. 2 is a block diagram illustrating a detailed configuration example of the motion information collecting circuitry 10 according to the first embodiment. As illustrated in FIG. 2, the motion information collecting circuitry 10 is connected to the motion information processing apparatus 20, and includes color image collecting circuitry 11, distance image collecting circuitry 12, sound recognizing circuitry 13, and motion information generating circuitry 14. Note that the configuration of the motion information collecting circuitry 10 illustrated in FIG. 2 is an example, and an embodiment is not limited to the example.

The color image collecting circuitry 11 captures a subject such as a person, an object in a space where rehabilitation is performed, and collects color image information. For example, the color image collecting circuitry 11 detects light reflected on a subject surface with a light-receiving element, and converts visible light into an electrical signal. Then, the color image collecting circuitry 11 generates one frame of color image information corresponding to a captured range by converting the electrical signal into digital data. This one frame of color image information includes, for example, captured time information, and information in which RGB (red, green, and blue) values are associated with pixels included in the one frame. The color image collecting circuitry 11 captures a moving image of the captured range by generating a plurality of continued frames of color image information from sequentially detected visible light. Note that the color image information generated by the color image collecting circuitry 11 may be output as a color image in which the RGB values of the pixels are arranged in a bitmap. Further, the color image collecting circuitry 11 includes a complementary metal oxide semiconductor (CMOS) or a charge coupled device (CCD), as the light-receiving element, for example.

The distance image collecting circuitry 12 captures a subject such as to person, an object in a space where rehabilitation is performed, and collects distance image information. For example, the distance image collecting circuitry 12 irradiates the neighborhood with infrared light, and detects a reflected wave that is an irradiation wave reflected on the subject surface, with a light-receiving element. Then, the distance image collecting circuitry 12 obtains a distance between the subject and the distance image collecting circuitry 12, based on a phase difference between the irradiation wave and the reflected wave, and a time from the irradiation to the detection, and generates one frame of distance image information corresponding to the captured range. This one frame of distance image information includes, for example, the captured time information, and information in which each pixel included in the captured range is associated with the distance between the subject and the distance image collecting circuitry 12 corresponding to the pixel. The distance image collecting circuitry 12 captures a moving image of the captured range by generating a plurality of continued frames of distance image information from sequentially detected reflected waves. Note that the distance image information generated by the distance image collecting circuitry 12 may be output as a distance image in which light and shade of colors according to the distances of the respective pixels is arranged in bitmap. Further, the distance image collecting circuitry 12 includes a CMOS or a CCD, as the light-receiving element, for example. This light-receiving element may be commonly used as the light-receiving element used in the color image collecting circuitry 11. Further, the unit of the distances calculated in the distance image collecting circuitry 12 is, for example, meter [m].

The sound recognizing circuitry 13 collects sounds in the neighborhood, and identifies a direction of a sound source and recognizes a sound. The sound recognizing circuitry 13 includes a microphone array provided with a plurality of microphones, and performs beam forming. The beam forming is a technology to selectively collect a sound from a specific direction. For example, the sound recognizing circuitry 13 identifies the direction of the sound source by the beam forming using the microphone array. Further, the sound recognizing circuitry 13 recognizes a word from the collected sounds using a known sound recognition technology. That is, the sound recognizing circuitry 13 generates information in which the word recognized by the sound recognition technology, a direction from which the word is brought out, and a time at which the word is recognized are associated with each other, as a sound recognition result.

The motion information generating circuitry 14 generates motion information that indicates a motion of a person, an object, or the like. The motion information generating circuitry 14 generates the motion information by capturing a motion (gesture) of a person as a series of a plurality of postures (pauses). To describe an outline, the motion information generating circuitry 14 first obtains coordinates of joints that form a skeleton of a human body from the distance image information generated by the distance image collecting circuitry 12 by pattern matching using a human body pattern. The coordinates of the joints obtained from the distance image information are values expressed in a coordinate system (hereinafter, called "distance image coordinate system") of distance image. Therefore, the motion information generating circuitry 14 next converts the coordinates of the respective joints in the distance image coordinate system into values expressed in a coordinate system (hereinafter, called "world coordinate system") in a three-dimensional space where rehabilitation is performed. The coordinates of the respective joints expressed in the world coordinate system serve as one frame of skeleton information. Further, a plurality of frames of the skeleton information is the motion information. Hereinafter, processing of the motion information generating circuitry 14 according to the first embodiment will be specifically described.

Figure 3B:
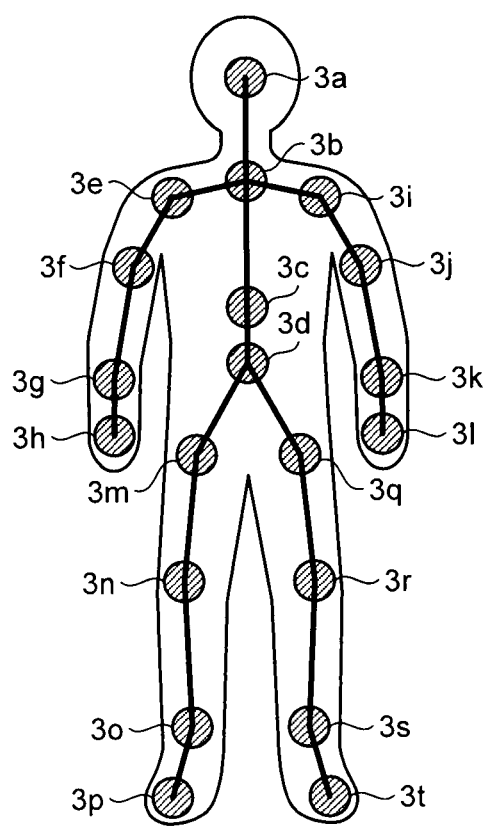
FIG. 3B is a diagram for describing the processing of the motion information generating circuitry according to the first embodiment.
Figure 3C:
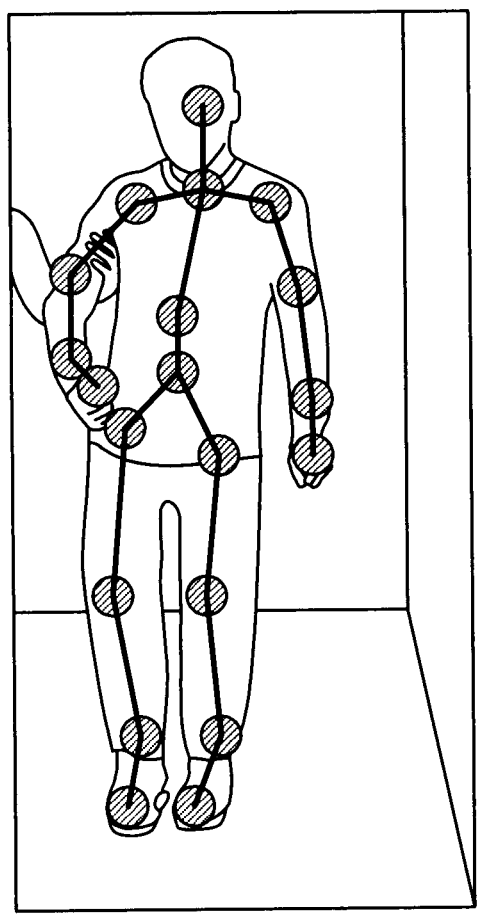
FIG. 3C is a diagram for describing the processing of the motion information generating circuitry according to the first embodiment.

FIGS. 3A to 3C are diagrams for describing processing of the motion information generating circuitry 14 according to the first embodiment. FIG. 3A illustrates an example of a distance image generated by the distance image collecting circuitry 12. Note that, in FIG. 3A, an image is expressed by line drawing for convenience of description. However, an actual distance image is an image or the like expressed by light and shade of a color according to a distance. In the distance image, each pixel includes a three-dimensional value in which a "pixel position X" in a right and left direction of the distance image, a "pixel position Y" in an up and down direction of the distance image, and a "distance Z" between a subject corresponding to the pixel and the distance image collecting circuitry 12, are associated with one another. Hereinafter, the values of the coordinates in the distance image coordinate system are written as three-dimensional values (X, Y, Z).

In the first embodiment, the motion information generating circuitry 14 stores human body patterns corresponding to various postures by learning, in advance. The motion information generating circuitry 14 acquires generated distance image information of each frame every time the distance image information is generated by the distance image collecting circuitry 12. Then, the motion information generating circuitry 14 performs the pattern matching using the human body pattern, for the acquired distance image information of each frame.

Here, the human body pattern will be described. FIG. 3B illustrates an example of the human body pattern. In the first embodiment, the human body pattern is a pattern used in the pattern matching with the distance image information, and thus expressed in the distance image coordinate system and including information of a surface of a human body (hereinafter, called "human body surface"), similar to a person visualized in the distance image. For example, the surface of a human body corresponds to a surface of a skin or clothes of the person. Further, as illustrated in FIG. 3B, the human body pattern includes information of joints that forms a skeleton of the human body. That is, in the human body pattern, relative positional relationship between the surface of the human body and the respective joints is known.

In the example illustrated in FIG. 3B, the human body pattern includes information of 20 points of joints from a joint 3*a* to joint 3*t*. Among the joints, the joint 3*a* corresponds to a head, a joint 3*b* corresponds to a central portion of both shoulders, a joint 3*c* corresponds to a waist, and a joint 3*d* corresponds to a central portion of a hip. Further, a joint 3*e* corresponds to a right shoulder, a joint 3*f* corresponds to a right elbow, a joint 3*g* corresponds to a right wrist, and a joint 3*h* corresponds to a right hand. Further, a joint 3*i* corresponds to a left shoulder, a joint 3*j* corresponds to a left elbow, a joint 3*k* corresponds to a left wrist, and a joint 3*l* corresponds to a left hand. Further, a joint 3*m* corresponds to a right hip, a joint 3*n* corresponds to a right knee, a joint 3*o* corresponds to a right ankle, and a joint 3*p* corresponds to a tarsus of a right foot. Further, a joint 3*q* corresponds to a left hip, a joint 3*r* corresponds to a left knee, a joint 3*s* corresponds to a left ankle, and a joint 3*t* corresponds to a tarsus of a left foot.

Note that, in FIG. 3B, the case where the human body pattern has the information of 20 points of joints has been described. However, an embodiment is not limited to the case, and positions and the number of joints may be arbitrarily set by an operator. For example, when only change of movements of the arms and feet is captured, the information of the joints 3*b* and 3*c*, of the joints 3*a* to 3*d*, may not be obtained. Further, when change of a movement of the right hand is captured in detail, not only the joint 3*h*, but also a joint of a finger of the right hand may be newly set. Note that, the joints 3*a*, 3*h*, 3*l*, 3*p*, and 3*t* of FIG. 3B are end portions of bones and thus are different from so-called joints. However, they are important points expressing positions and directions of bones. Therefore, here, they are described as joints for convenience of description.

The motion information generating circuitry 14 performs the pattern matching with the distance image information of each frame using the human body pattern. For example, the motion information generating circuitry 14 extracts a person in a certain posture from the distance image information by performing pattern matching between the human body surface of the human body pattern illustrated in FIG. 3B, and the distance image illustrated in FIG. 3A. In this way, the motion information generating circuitry 14 obtains coordinates on the human body surface of the person visualized in the distance image. Further, as described above, the relative positional relationship between the human body surface and the respective joints are known in the human body pattern. Therefore, the motion information generating circuitry 14 calculates coordinates of the respective joints in the person from the coordinates on the human body surface, of the person visualized in the distance image. In this way, as illustrated in FIG. 3C, the motion information generating circuitry 14 acquires the coordinates of the respective joints that form skeleton of the human body from the distance image information. Note that the coordinates of the respective joints obtained here are coordinates in a distance coordinate system.

Note that, when performing the pattern matching, the motion information generating circuitry 14 may auxiliary use information that indicates positional relationship among the joints. The information that indicates the positional relationship among the joints includes, for example, coupling relationship between joints (for example, "the joint 3*a* and the joint 3*b* are coupled" or the like), the ranges of motion of the respective joints, and the like. A joint is a portion that couples two or more bones. An angle made by bones is changed according to change of a posture, and the range of motion differs according to a joint. For example, the range of motion is expressed by a maximum value, a minimum value, or the like of the angle made by bones coupled by each joint. For example, when learning the human body pattern, the motion information generating circuitry 14 also learns the ranges of motion of the respective joints, and stores the ranges of motion in association with the respective joints.

Following that, the motion information generating circuitry 14 converts the coordinates of the respective joints in the distance image coordinate system into values expressed in the world coordinate system. The world coordinate system is a coordinate system in a three-dimensional space where rehabilitation is performed, and is a coordinate system in which the position of the motion information collecting circuitry 10 is the origin, a horizontal direction is an x axis, a vertical direction is a y axis, and a direction perpendicular to an xy plane is a z axis, for example. Note that values of coordinates in the z axis direction may be called "depth".

Processing to convert the coordinates from the distance image coordinate system into the world coordinate system will be described. In the first embodiment, the motion information generating circuitry 14 stores a conversion formula for converting the coordinates from the distance image coordinate system to the world coordinate system. For example, this conversion formula outputs the coordinates in the world coordinate system using the coordinates in the distance image coordinate system, and an incident angle of reflection light corresponding to the coordinates as inputs. For example, the motion information generating circuitry 14 inputs coordinates (X1, Y1, Z1) of a certain joint, and the incident angle of reflection light corresponding to the coordinates to the conversion formula to convert the coordinates (X1, Y1, Z1) of the certain joint into coordinates (x1, y1, z1) in the world coordinate system. Note that, since corresponding relationship between the coordinates in the distance image coordinate system, and the incident angle of reflection light is known, the motion information generating circuitry 14 can input the incident angle corresponding to the coordinates (X1, Y1, Z1) to the conversion formula. Here, the case in which the motion information generating circuitry 14 converts the coordinates in the distance image coordinate system into the coordinates in the world coordinate system has been described. However, the coordinates in the world coordinate system can be converted into coordinates in the distance coordinate system.

Then, the motion information generating circuitry 14 generates skeleton information from the coordinates of the respective joints expressed in the world coordinate system. FIG. 4 is a diagram illustrating an example of the skeleton information generated by the motion information generating circuitry 14. The skeleton information of each frame includes captured time information of the frame, and the coordinates of the respective joints. For example, as illustrated in FIG. 4, the motion information generating circuitry 14 generates the skeleton information in which joint identification information and coordinate information are associated with each other. Note that, in FIG. 4, illustration of the captured time information is omitted. The joint identification information is identification information for identifying the joints, and is set in advance. For example, joint identification information "3*a*" corresponds to the head, and joint identification information "3*b*" corresponds to the central portion of both shoulders. The same applies to other pieces of the joint identification information, and each of the joint identification information indicates each corresponding joint. Further, the coordinate information indicates the coordinates of the respective joints in each frame, in the world coordinate system.

In the first row of FIG. 4, the joint identification information "3*a*" and the coordinate information "(x1, y1, z1)" are associated with each other. That is, the skeleton information of FIG. 4 indicates that the head exists in the position of the coordinates (x1, y1, z1) in a certain frame. Further, in the second row of FIG. 4, the joint identification information "3*b*" and coordinate information "(x2, y2, z2)" are associated with each other. That is, the skeleton information of FIG. 4 indicates that the central portion of both shoulders exists in the position of the coordinates (x2, y2, z2) in the certain frame. Further, the same applies to other joints, and the skeleton information indicates that the respective joints exist in the positions expressed by respective coordinates in the certain frame.

As described above, the motion information generating circuitry 14 performs the pattern matching with respect to the distance image information of each frame every time acquiring the distance image information of each frame from the distance image collecting circuitry 12, and converts the coordinates from the distance image coordinate system into the world coordinate system, thereby to generate the skeleton information of each frame. Then, the motion information generating circuitry 14 transmits the generated skeleton information of each frame to the motion information processing apparatus 20, as motion information.

Note that processing of the motion information generating circuitry 14 is not limited to the above-described technique. For example, in the above description, the technique in which the motion information generating circuitry 14 performs the pattern matching using the human body pattern has been described. However, a technique is not limited to the embodiment. For example, a technique to perform the pattern matching using patterns of different portions in place of the human body pattern or together with the human body pattern may be performed.

Further, in the above description, the technique in which the motion information generating circuitry 14 obtains the coordinates of the respective joints from the distance image information has been described. However, an embodiment is not limited to the technique. For example, a technique in which the motion information generating circuitry 14 obtains the coordinates of the respective joints using color image information together with the distance image information may be used. In this case, for example, the motion information generating circuitry 14 performs the pattern matching using the human body pattern and the color image information expressed in a coordinate system of a color image, and obtains coordinates of the human body surface from the color image information. In the coordinate system of a color image does not include the information of the "distance Z" in the distance image coordinate system. Therefore, the motion information generating circuitry 14 obtains the information of the "distance Z" from the distance image information, for example, and obtains the coordinates of the respective joints in the world coordinate system by calculation processing using these two pieces of information.

Further, the motion information generating circuitry 14 transmits the color image information of a plurality of frames generated by the color image collecting circuitry 11 to the motion information processing apparatus 20, as moving image information. Further, the motion information generating circuitry 14 appropriately transmits the distance image information generated by the distance image collecting circuitry 12 and the sound recognition result output by the sound recognizing circuitry 13 to the motion information processing apparatus 20, as needed. Note that a pixel position of the color image information and a pixel position of the distance image information can be associated with each other in advance according to positions and capturing directions of the color image collecting circuitry 11 and the distance image collecting circuitry 12. Therefore, the pixel position of the color image information and the pixel position of the distance image information can be associated with the world coordinate system calculated by the motion information generating circuitry 14. Further, the height or the length of each portion of the body (the length of the arm or the length of an abdomen), and a distance between two pixels specified on the color image can be obtained using the association and a distance [m] calculated by the distance image collecting circuitry 12. Further, similarly, captured time information of the color image information and captured time information of the distance image information can be associated with each other in advance. Further, the motion information generating circuitry 14 can refer to the sound recognition result and the distance image information, and when there is the joint 3a in the vicinity of the direction from which a word is brought out, a sound of which has been recognized at a certain time, the motion information generating circuitry 14 can output the word as a word uttered by the person that includes the joint 3a. Further, the motion information generating circuitry 14 appropriately transmits the information that indicates positional relationship among the joints to the motion information processing apparatus 20, as needed.

Note that the case in which a motion of a single person is detected by the motion information collecting circuitry 10 has been described here. However, an embodiment is not limited to the case. The motion information collecting circuitry 10 may detect motions of a plurality of persons as long as the motions are included in the captured range of the motion information collecting circuitry 10. Note that, when a plurality of persons is captured in the distance image information of the same frame, the motion information collecting circuitry 10 associates the skeleton information of the plurality of persons generated from the distance image information of the same frame with one another, and outputs the associated information to the motion information processing apparatus 20, as the motion information.

Further, a configuration of the motion information collecting circuitry 10 is not limited to the above-described configuration. For example, when generating the motion information by detecting a motion of a person by another motion capture, such as an optical system, a mechanical system, or a magnetic system, the motion information collecting circuitry 10 may not necessarily include the distance image collecting circuitry 12. In such a case, the motion information collecting circuitry 10 includes a marker to be mounted on the human body and a sensor that detects the marker, as a motion sensor, in order to detect the motion of the person. Then, the motion information collecting circuitry 10 detects the motion of the person using the motion sensor, and generates the motion information. Further, the motion information collecting circuitry 10 associates the pixel position of the color image information and the coordinates of the motion information using the position of the marker included in the image captured by the color image collecting circuitry 11, and then appropriately outputs the associated information to the motion information processing apparatus 20, as needed. Further, for example, the motion information collecting circuitry 10 may not include the sound recognizing circuitry 13 when not outputting the sound recognition result to the motion information processing apparatus 20.

Further, in the above-described embodiment, the motion information collecting circuitry 10 outputs the coordinates of the world coordinate system, as the skeleton information. However, the embodiment is not limited thereto. For example, the motion information collecting circuitry 10 may output the coordinates in the distance image coordinate system before conversion, and the conversion from the distance image coordinate system into the world coordinate system may be performed at the side of the motion information processing apparatus 20, as needed.

Referring back to the description of FIG. 1, the motion information processing apparatus 20 processes various types of information for assisting rehabilitation. The motion information processing apparatus 20 is an information processing apparatus such as a computer, or a workstation.

For example, the motion information processing apparatus 20 accepts the moving image information and the motion information transmitted by the motion information generating circuitry 14. Then, the motion information processing apparatus 20 outputs the accepted moving image information and motion information to a monitor, a speaker, and the like, and transmits the accepted moving image information and motion information to the medical-use image storage apparatus 40.

Further, for example, the motion information processing apparatus 20 accepts the distance image information and the sound recognition result transmitted by the motion information generating circuitry 14. Then, the motion information processing apparatus 20 appropriately outputs the accepted distance image information and sound recognition result to a monitor, a speaker, and the like, and appropriately transmits the accepted distance image information and sound recognition result to the medical-use image storage apparatus 40.

The medical-use image diagnostic apparatus 30 is a apparatus such as an X-ray diagnostic apparatus, an X-ray computed tomography (CT) apparatus, a magnetic resonance imaging (MRI) apparatus, a ultrasonic diagnostic apparatus, a single photon emission computed tomography (SPECT) apparatus, a positron emission computed tomography (PET) apparatus, a SPECT-CT apparatus in which a SPECT apparatus and an X-ray CT apparatus are integrated, a PET-CT apparatus in which a PET apparatus and an X-ray CT apparatus are integrated, or a specimen inspection apparatus. For example, the medical-use image diagnostic apparatus 30 captures a test object such as a patient according to an operation from a film operator who captures the test object such as a patient, and generates medical-use image information. Then, the medical-use image diagnostic apparatus 30 transmits the generated medical-use image information to the medical-use image storage apparatus 40.

The medical-use image storage apparatus 40 stores the various types of information for assisting rehabilitation. For example, the medical-use image storage apparatus 40 includes a database in which the image information is stored, and stores the various types of information transmitted by the motion information processing apparatus 20 and the medical-use image diagnostic apparatus 30, in the database.

For example, the medical-use image storage apparatus 40 stores the moving image information and the motion information transmitted by the motion information processing apparatus 20 in association with each other, for each target person. The moving image information is the color image information of the plurality of frames generated by the color image collecting circuitry 11, and is information of a moving image of a captured target person who undergoes rehabilitation, for example. Further, the moving image information includes information that indicates a type of the rehabilitation (for example, walking training, training of joint movable range, or the like) undergone by the captured target person, as incidental information. Further, the motion information is the skeleton information corresponding to each frame of the moving image information, and indicates a motion of the target person captured in the moving image information, for example.

The motion information display apparatus 100 displays the various types of information for assisting rehabilitation. For example, the motion information display apparatus 100 obtains the moving image information and the motion information from the medical-use image storage apparatus 40, and displays the acquired information.

Figure 5:
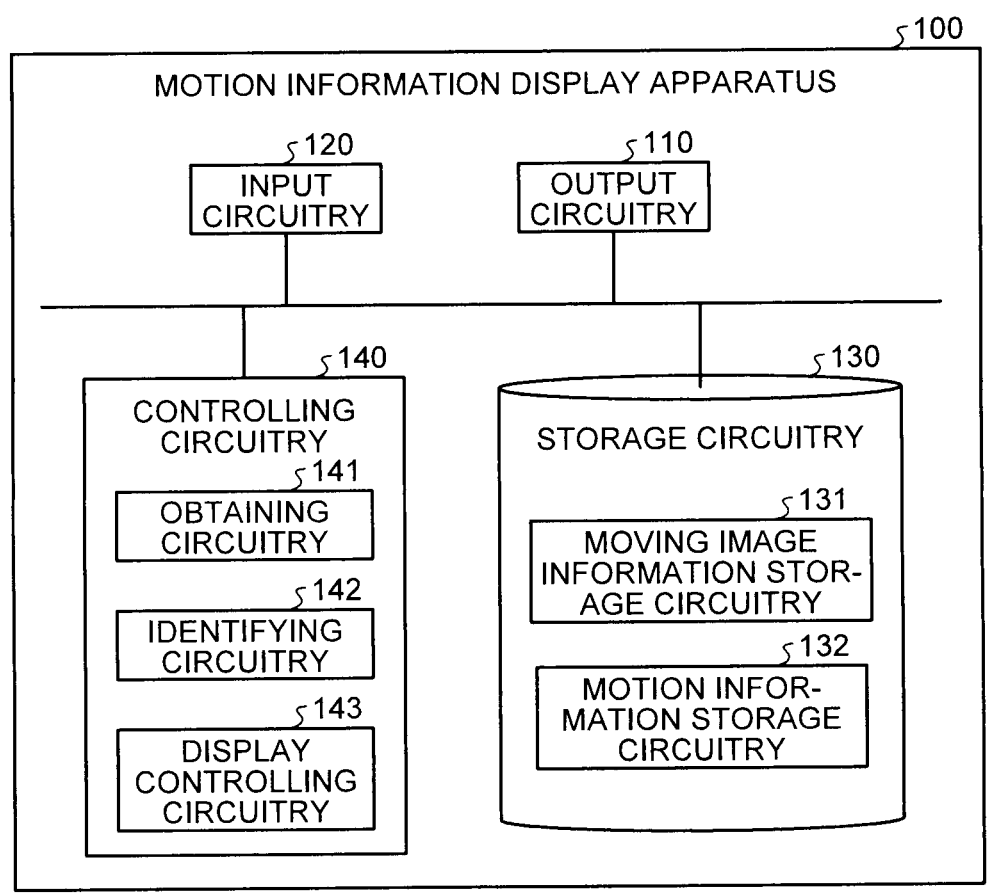
FIG. 5 is a block diagram illustrating a detailed configuration example of a motion information display apparatus according to the first embodiment.

FIG. 5 is a block diagram illustrating a detailed configuration example of the motion information display apparatus 100 according to the first embodiment. As illustrated in FIG. 5, the motion information display apparatus 100 includes output circuitry 110, input circuitry 120, storage circuitry 130, and controlling circuitry 140.

Here, the motion information display apparatus 100 according to the first embodiment can appropriately display the moving image of captured rehabilitation, by processing described below. For example, when arranging and displaying a plurality of moving images of walking training, the motion information display apparatus 100 can display the moving images, synchronizing timings of the motions.

For example, walking from standing upright is performed by repetition of motions below:

(1) Put the right foot forward.
(2) Allow the right foot to land on a floor surface.
(3) Shift the center of gravity of the boy toward the right foot, and puts the weight on the right foot.
(4) Remove the weight from the left foot.
(5) Hit the floor surface with the left foot.
(6) Put the left foot farther forward than the right foot.
(7) Allow the left foot to land on the floor surface.
(8) Shift the center of gravity of the body toward the left foot, and puts the weight on the left foot.
(9) Remove the weight from the right foot.
(10) Hit the floor surface with the right foot.
(11) Put the right foot farther forward than the left foot.

Hereinafter, returning to (2), and the motions from (2) to (11) are repeated until the end of walking. Note that, in the walking, both feet cannot come off the ground at the same time, and putting the arm forward, which is at the opposite side to the foot put forward, maintains the balance of the center of gravity of the body.

Here, for example, it can be considered that, when two moving images are displayed and compared, that is, when a moving image in which walking of a healthy person is captured and a moving image in which walking training of a target person is captured are displayed and compared, it is useful to display the moving images using predetermined timings. As an example, it can be considered that, when timings at which the right feet land on the ground first time are caused to accord with each other and the two moving images are played back at the same time, walking speeds of the healthy person and the target person walk can be compared. Further, as another example, it can be considered that, when landing timings of the right feet are caused to accord with each other in the two moving images, walking forms of the healthy person and the target person can be compared. Therefore, the motion information display apparatus 100 can display a plurality of moving images using the landing timings of the right feet by processing described below, when displaying two moving images in which the walking training is captured.

Note that, in the first embodiment, a case of using a timing at which the right foot lands on the ground will be described. However, an embodiment is not limited to the case. For example, in the embodiment, a timing at which another motion is performed, such as a timing at which the left foot hits the floor surface, may be used. Further, an embodiment is not limited to the case where the moving image of the walking training is displayed, and may be applied to a case where a moving image of another training such as the training of joint movable range is displayed, for example. Further, an embodiment is not limited to the case where the healthy person and the target person are compared, and for example, a current target person and a past target person may be compared. To be specific, in the embodiment, the target person before an operation and the target person after the operation may be compared, or the target person immediately after the operation and the target person after elapse of several months after the operation may be compared. Further, in the embodiment, three or more moving images may be compared. Further, in the embodiment, a plurality of moving images may be arranged and displayed in the horizontal direction or in the vertical direction.

The output circuitry 110 outputs the various types of information for assisting rehabilitation. For example, the output circuitry 110 displays a graphical user interface (GUI) for allowing an operator who operates the motion information display apparatus 100 to input various requests using the input circuitry 120, displays an output image generated in the motion information display apparatus 100, and outputs a warning sound. For example, the output circuitry 110 is a monitor, a speaker, a headphone, or a headphone portion of a head set.

The input circuitry 120 accepts an input of the various types of information for assisting rehabilitation. For example, the input circuitry 120 accepts an input of various types of requests from the operator of the motion information display apparatus 100, and transfers the accepted various types of requests to the motion information display apparatus 100. For example, the input circuitry 120 is a mouse, a keyboard, a touch command screen, a trackball, a microphone, a microphone portion of a head set.

The storage circuitry 130 includes moving image information storage circuitry 131 and motion information storage circuitry 132. For example, the storage circuitry 130 is a semiconductor memory element such as a random access memory (RAM) or a flash memory, or a storage device such as a hard disk device or an optical device.

The moving image information storage circuitry 131 stores the moving image information to be displayed. The moving image information is the color image information of the plurality of frames, and is the moving image information of the captured target person who undergoes the rehabilitation, for example. Further, the moving image information includes the information that indicates a type of the rehabilitation (for example, walking training, training of joint movable range, or the like) undergone by the captured target person, as the incidental information. For example, the moving image information storage circuitry 131 stores the moving image information obtained from the medical-use image storage apparatus 40 by obtaining circuitry 141 described below. Note that, the moving image information stored in the moving image information storage circuitry 131 may be acquired from the motion information processing apparatus 20.

The motion information storage circuitry 132 stores the motion information corresponding to the moving image information stored in the moving image information storage circuitry 131. The motion information is the skeleton information corresponding to each frame of the moving image information, and indicates, for example, a motion of the target person captured in the moving image information. For example, the motion information storage circuitry 132 stores the motion information obtained from the medical-use image storage apparatus 40 by the obtaining circuitry 141. Note that, the motion information stored in the motion information storage circuitry 132 may be acquired from the motion information processing apparatus 20.

The controlling circuitry 140 includes obtaining circuitry 141, identifying circuitry 142, and display controlling circuitry 143. For example, the controlling circuitry 140 can be realized by an integrated circuit such as an application specific integrated circuit (ASIC) or a field programmable gate array (FPGA), or can be realized by execution of a predetermined program by a central processing unit (CPU).

The obtaining circuitry 141 obtains a plurality of pieces of the moving image information, and the motion information that indicates a motion of a subject included in each of the moving image information.

For example, the obtaining circuitry 141 accesses the medical-use image storage apparatus 40, and accepts an input for specifying a target person ID that identifies the target person, from the operator through the input circuitry 120. Following that, the obtaining circuitry 141 displays a list of the moving image information that can be played back about the target person of the specified target person ID, of the moving image information stored in the medical-use image storage apparatus 40 to the output circuitry 110. Then, the obtaining circuitry 141 accepts an input for selecting the moving image information to be displayed from the displayed list, from the operator through the input circuitry 120. Then, the obtaining circuitry 141 obtains the selected one piece of the moving image information, and the motion information corresponding to the moving image information, from the medical-use image storage apparatus 40, and stores the acquired moving image information and motion information in the moving image information storage circuitry 131 and the motion information storage circuitry 132, respectively. Note that the obtaining circuitry 141 repeats the above-described processing as needed, thereby to obtain the repeated number of pieces of the moving image information and the motion information, as information to be displayed.

The identifying circuitry 142 identifies the frame corresponding to a timing of a predetermined motion performed in the rehabilitation, from each frame group included in each of the moving image information, based on the motion information. For example, the identifying circuitry 142 accepts an input for specifying the purpose of the rehabilitation, from the operator through the input circuitry 120. The identifying circuitry 142 identifies the frame corresponding to the timing of the predetermined motion according to the specified purpose of the rehabilitation.

Figure 6A:
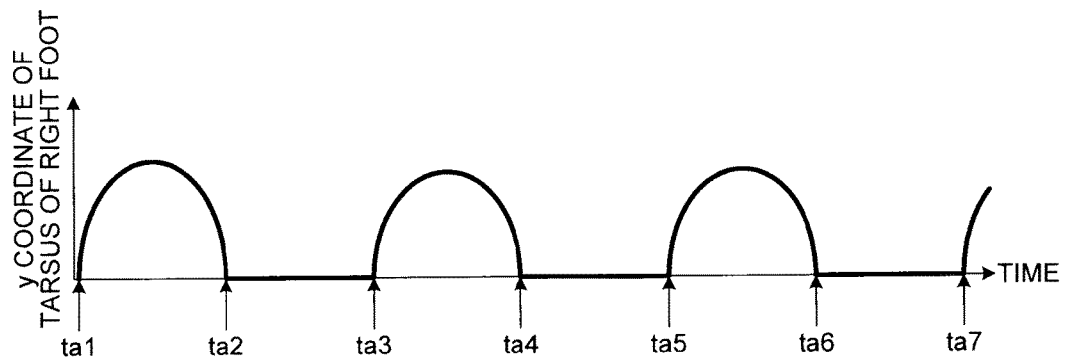
FIG. 6A is a diagram for describing processing of identifying circuitry according to the first embodiment.
Figure 6B:
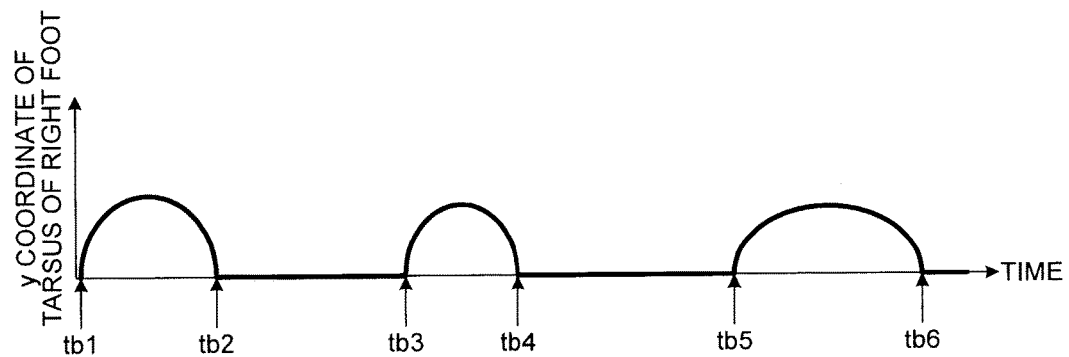
FIG. 6B is a diagram for describing the processing of the identifying circuitry according to the first embodiment.

FIGS. 6A and 6B are diagrams for describing processing of the identifying circuitry 142 according to the first embodiment. In FIGS. 6A and 6B, a case in which the identifying circuitry 142 specifies a timing at which the right foot lands on the ground from the moving image of the walking training will be described. Note that FIG. 6A is a graph illustrating change with time of a y coordinate of the tarsus of the right foot in the walking of the healthy person, and FIG. 6B is a graph illustrating change with time of a y coordinate of the tarsus of the right foot in the walking of the target person. In FIGS. 6A and 6B, the horizontal axes represent time, and the vertical axes represent a value of the y coordinate of the tarsus of the right foot. That is, y=0 indicates that the tarsus of the right foot lands on the floor surface.

FIGS. 6A and 6B exemplarily illustrate the walking from standing upright. That is, ta1 of FIG. 6A corresponds to a timing at which the healthy person puts the right foot forward. Further, ta2, ta4, and tab correspond to a timing at which the healthy person allows the right foot to land on the floor surface. Further, ta3, ta5, and ta7 correspond to a timing at which the healthy person hits on the floor surface with the right foot. Further, tb1 of FIG. 6B corresponds to a timing at which the target person puts the right foot forward. Further, tb2, tb4, and tb6 correspond to a timing at which the target person allows the right foot to land on the floor surface. Further, tb3 and tb5 correspond to a timing at which the target person hits on the floor surface with the right foot. As illustrated in FIGS. 6A and 6B, the healthy person walks more regularly and with a higher pace than the target person, while the target person walks irregularly and with a slower pace than the healthy person. Note that, hereinafter, the timing at which the foot lands on the ground may be abbreviated as "landing timing".

Here, a case where improvement of the walking speed of the target person is specified as the purpose of the rehabilitation will be described. In this case, the identifying circuitry 142 accepts an input for specifying the improvement of the walking speed of the target person, from the operator. When the improvement of the walking speed has been specified, the identifying circuitry 142 identifies a frame corresponding to the first landing timing of the right foot, from each frame group included in each of the moving image information obtained by the obtaining circuitry 141. To be specific, as illustrated in FIG. 6A, the identifying circuitry 142 refers to the motion information of the healthy person, and identifies the first frame from a plurality of frames in which the y coordinate of the tarsus (joint 3p) of the right foot of the healthy person is 0 for a fixed period. In the example illustrated in FIG. 6A, the identifying circuitry 142 identifies frames respectively corresponding to ta2, ta4, and ta6, as the landing timings of the right foot of the healthy person. Then, the identifying circuitry 142 identifies the frame corresponding to ta2 in the earliest time, from the identified frames respectively corresponding to ta2, ta4, and ta6, as the first landing timings of the right foot. Further, as illustrated in FIG. 6B, the identifying circuitry 142 identifies a frame corresponding to tb2, as the first landing timing of the right foot of the target person, by similar processing.

Following that, the identifying circuitry 142 identifies the size of the person captured in each of the moving image information. For example, the identifying circuitry 142 identifies a ratio occupied by the person to the number of pixels of the color image in the up and down direction, in the frame corresponding to the identified landing timing, as the size of the person. To be specific, the identifying circuitry 142 obtains the coordinates of the head (joint 3a) and the tarsus of the right foot (joint 3p) from the skeleton information of the frames respectively corresponding to ta2 and tb2. The identifying circuitry 142 calculates pixel positions respectively corresponding to the obtained coordinates of the head and the tarsus of the right foot. The identifying circuitry 142 calculates the ratio occupied by the number of pixels from the head to the tarsus of the right foot to the number of pixels of the color image in the up and down direction, as the size of the person. In this way, the identifying circuitry 142 identifies the size of the person captured in each of the moving image information.

Further, a case where improvement of the walking form of the target person is specified as the purpose of rehabilitation will be described. In this case, the identifying circuitry 142 accepts an input for specifying the improvement of the walking form of the target person, from the operator. When the improvement of the walking form has been specified, the identifying circuitry 142 identifies frames corresponding to all landing timings of the right foot, from each frame group included in each of the moving image information obtained by the obtaining circuitry 141. To be specific, as illustrated in FIG. 6A, the identifying circuitry 142 refers to the motion information of the healthy person, and identifies the first frame from a plurality of frames in which the y coordinate of the tarsus (joint 3p) of the right foot of the healthy person is 0 for a fixed period. In the example illustrated in FIG. 6A, the identifying circuitry 142 identifies the frames respectively corresponding to ta2, ta4, and ta6, as the landing timings of the right foot of the healthy person. Further, as illustrated in FIG. 6B, the identifying circuitry 142 identifies frames respectively corresponding to tb2, tb4, and tb6, as all landing timings of the right foot of the target person, by similar processing.

Following that, the identifying circuitry 142 identifies the size of the person captured in each of the moving image information. For example, the identifying circuitry 142 identifies a ratio occupied by the person to the number of pixels of the color image in the up and down direction, in the frame corresponding to the identified landing timing, as the size of the person. Here, when there is a plurality of identified landing timings, the identifying circuitry 142 identifies the size of the person using the first landing timing. To be specific, the identifying circuitry 142 identifies the size of the person by processing similar to the above-described processing.

Note that the purpose of rehabilitation is not limited to the above-described examples, and is appropriately set according to the type of the rehabilitation and a state of the target person. Then, processing for identifying an appropriate timing according to the set purpose is set to the identifying circuitry 142 in advance.

A case where an effect of an operation is confirmed by how much the walking speed of the target person is improved before and after the operation will be described as an embodiment. In this case, the identifying circuitry 142 accepts an input for specifying improvement of the walking speed of the target person, from the operator. When the improvement of the walking speed has been specified, the identifying circuitry 142 identifies frames corresponding to the first landing timing of the right foot, from respective frame groups included in the moving image information before the operation and the moving image information after the operation.

The display controlling circuitry 143 performs display control of a plurality of pieces of the moving image information using frames corresponding to a timing of a predetermined motion. For example, when arranging and displaying a plurality of moving images of the walking training, the display controlling circuitry 143 performs the display control of a plurality of pieces of the moving image information using the frames corresponding to the landing timing of the right foot identified by the identifying circuitry 142.

Figure 7:
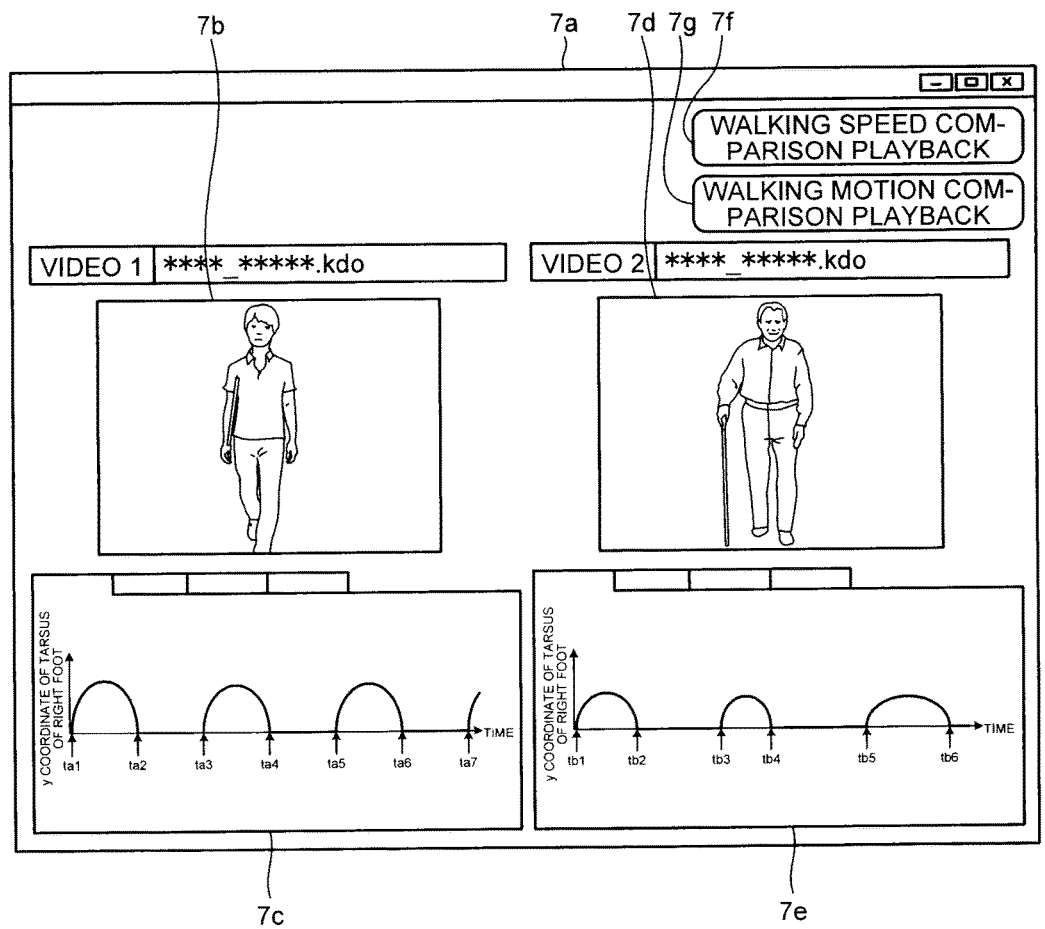
FIG. 7 is a diagram for describing processing of display controlling circuitry according to the first embodiment.

FIG. 7 is a diagram for describing processing of the display controlling circuitry 143 according to the first embodiment. FIG. 7 illustrates an example of a display screen 7a displayed in the output circuitry 110 by the display controlling circuitry 143. The display screen 7a includes a region 7b where the moving image information of the healthy person is displayed, a region 7c where a graph that indicates change with time of the y coordinate of the tarsus of the right foot of the healthy person is displayed, a region 7d where the moving image information of the target person is displayed, and a region 7e where a graph that indicates change with time of the y coordinate of the tarsus of the right foot of the target person is displayed. Further, the display screen 7a includes a walking speed comparison playback button 7f for specifying the improvement of the walking speed of the target person as the purpose of rehabilitation, and a walking motion comparison playback button 7g for specifying the improvement of the walking form of the target person.

Here, a case where the improvement of the walking speed of the target person is specified as the purpose of rehabilitation will be described. For example, the identifying circuitry 142 accepts information that indicates that the walking speed comparison playback button 7f has been pressed by the operator, from the input circuitry 120. Then, the display controlling circuitry 143 performs playback control so as to cause the sizes of the target person and start timings in the moving image information to accord with each other. To be specific, the display controlling circuitry 143 enlarges or reduces the moving image information of the healthy person and the moving image information of the target person such that the healthy person and the target person can have nearly the same size, using the sizes of the persons identified by the identifying circuitry 142. Following that, the display controlling circuitry 143 plays back these two pieces of moving image information at the same time such that the moving image information of the healthy person is started from the frame corresponding to ta2, and the moving image information of the target person is started from the frame corresponding to tb2.

Further, for example, the case where an effect of an operation is confirmed by how much the walking speed of the target person is improved before and after the operation will be described. In this case, for example, the identifying circuitry 142 accepts the information that indicates that the walking speed comparison playback button 7f has been pressed by the operator, from the input circuitry 120. Then, the display controlling circuitry 143 performs the playback control so as to cause the sizes of the target person and the start timings of the moving image information before the operation and the moving image information after the operation to accord with each other.

Further, a case where the improvement of the walking form of the target person is specified as the purpose of rehabilitation will be described. For example, the display controlling circuitry 143 accepts information that indicates that the walking motion comparison playback button 7g has been pressed by the operator, from the input circuitry 120. Then, the display controlling circuitry 143 performs the playback control so as to cause the sizes of the target person and the landing timings in the moving image information to accord with each other. To be specific, the display controlling circuitry 143 enlarges or reduces the moving image information of the healthy person and the moving image information of the target person such that the healthy person and the target person can have nearly the same size, using the sizes of the persons identified by the identifying circuitry 142. Following that, the display controlling circuitry 143 synchronizes the landing timings of the healthy person with the landing timings of the target person, and plays back the moving image information. To be more specific, since the number of frames from tb1 to tb2 is smaller than the number of frames from ta1 to ta2, the display controlling circuitry 143 partially interpolates frames from tb1 to tb2. Accordingly, the display controlling circuitry 143 plays back the moving image information so as to display the frames corresponding to ta2 and tb2 at the same time. Further, since the number of frames from tb2 to tb4 is larger than the number of frames from ta2 to ta4, the display controlling circuitry 143 partially thins out the frames from tb2 to tb4. Accordingly, the display controlling circuitry 143 plays back the moving image information so as to display the frames corresponding to ta4 and tb4 at the same time. As described above, the display controlling circuitry 143 plays back the moving image information so as to cause the respective landing timings to accord with each other.

Note that a method of synchronizing and playing back the moving images by the display controlling circuitry 143 is not limited to the above-described method. For example, when synchronizing ta2 and tb2, the display controlling circuitry 143 may temporarily stop the moving image information of the target person at the frame corresponding to tb2, which is played back first, until the frame corresponding to ta2 is played back in the moving image information of the healthy person.

Note that, in the above description, the case in which the start timings to play back the moving images are caused to accord with each other using the first landing timings has been described. However, an embodiment is not limited to the example. For example, in an embodiment, the start timings can be caused to accord with each other using the second or third landing timings. In this case, the moving images are played back at a normal speed until the second or third landing timing. Further, in an embodiment, for example, the second landing timing in one moving image and the third landing timing in the other moving image, of two moving images, may be caused to accord with each other.

Further, in the above description, the case in which all of playback times of the moving images are synchronized has been described. However, an embodiment is not limited to the case. For example, only fixed times of the playback times may be synchronized, and times before and after the fixed times may be displayed without being synchronized.

Next, a processing procedure of the motion information display apparatus 100 according to the first embodiment will be described with reference to FIG. 8. FIG. 8 is a flowchart for describing an example of a processing procedure of the motion information display apparatus 100 according to the first embodiment.

As illustrated in FIG. 8, when a plurality of pieces of moving image information has been selected by the operator (Yes at step S101), the obtaining circuitry 141 obtains the selected pieces of moving image information, and corresponding motion information (step S102). Note that the obtaining circuitry 141 is in a stand-by state until the plurality of pieces of moving image information is selected (No at step S101).

Following that, the identifying circuitry 142 accepts the information that indicates that the playback button has been pressed (step S103). When the walking speed comparison playback button has been pressed at step S103, the identifying circuitry 142 identifies a frame corresponding to the landing timing of the right foot at a point of time, based on each motion information obtained by the obtaining circuitry 141 (step S104). Following that, the identifying circuitry 142 identifies the size of the person captured in each of the moving image information (step S105). Then, the display controlling circuitry 143 performs the playback control so as to cause the sizes of the target person and the start timings of the moving image information to accord with each other (step S106), and terminates the processing.

Further, when the walking motion comparison playback button has been pressed at step S103, the identifying circuitry 142 identifies frames corresponding to all landing timings of the right foot, based on the moving information obtained by the obtaining circuitry 141 (step S107). Following that, the identifying circuitry 142 identifies the size of the person captured in each of the moving image information (step S108). Then, the display controlling circuitry 143 performs the playback control so as to cause the sizes of the target person and the landing timings of the moving image information to accord with each other (step S109), and terminates the processing.

Note that a processing procedure is not limited to the above-described processing procedure. For example, there is a case where the information that indicates the purpose of rehabilitation is stored in a rehabilitation electronic medical record server in association with the target person ID. In such a case, the identifying circuitry 142 obtains the information that indicates the purpose of rehabilitation from the rehabilitation electronic medical record server using the target person ID. Then, the identifying circuitry 142 may automatically select and execute the processing of step S104 or the processing of step S107 by using the obtained information that indicates the purpose of rehabilitation, even if the playback button is not pressed, which is the processing of step S103.

As described above, the motion information display apparatus 100 according to the first embodiment obtains a plurality of pieces of moving image information, and motion information that indicates a motion of a subject included in each of the moving image information. Then, the motion information display apparatus 100 identifies a frame corresponding to a timing of a predetermined motion performed in the rehabilitation, from each frame group included in each of the moving image information, based on the motion information. Then, the motion information display apparatus 100 performs the display control of the plurality of pieces of moving image information using the frame corresponding to a timing of a predetermined motion. Therefore, the motion information display apparatus 100 can appropriately display the moving image of the captured rehabilitation.

For example, when displaying and comparing walking of the healthy person and walking of the target person, the motion information display apparatus 100 according to the first embodiment causes timings at which the right feet land on the ground for the first time to approximately accord with each other, and plays back the timings, thereby to display and compare the walking speeds of the healthy person and the target person.

Further, for example, when displaying and comparing the walking of the healthy person and the walking of the target person, the motion information display apparatus 100 according to the first embodiment causes the timings at which the right feet land on the ground to approximately accord with each other (synchronizes landing periods of the right feet), thereby to display and compare the walking forms of the healthy person and the target person.

Further, for example, in evaluation of an outcome of the rehabilitation by a doctor or a physical therapist, the motion information display apparatus 100 can compare the outcome by a display method according to an evaluation purpose.

Second Embodiment

In the first embodiment, the case in which the moving image of the walking training is displayed has been described. However, an embodiment is not limited to the case. For example, an embodiment may be applied to a case where a moving image of another training, such as training of joint movable range, is displayed. Therefore, in a second embodiment, a case where a motion information display apparatus 100 displays a moving image of training of joint movable range will be described.

Here, the training of joint movable range is training for enlarging a movable range of a joint. For example, the training of joint movable range of a right elbow is to train how much a joint $3f$ of FIG. 3B can be moved. That is, the training of joint movable range of a right elbow is training to repeat a motion (bending and stretching) of operating the right elbow (the joint $3f$) without changing the position of an upper arm (from a joint $3e$ to the joint $3f$) having a state in which the right arm (form the joint $3e$ to a joint $3g$) is stretched straight, as a reference position, and bringing a right wrist (the joint $3g$) close to a right shoulder (the joint $3e$). In the training of joint movable range, an angle (the joint movable range) made by a front arm (from the joint $3f$ to the joint $3g$) before movement and the front arm after the joint $3g$) movement is used as an index of evaluation, for example.

A motion information display apparatus 100 according to the second embodiment has a configuration similar to the motion information display apparatus 100 illustrated in FIG. 5, and a part of processing in identifying circuitry 142 and display controlling circuitry 143 is different. Therefore, in the second embodiment, the point different from the first embodiment will be mainly described, and points having functions similar to the configurations described in the first embodiment are denoted with the same reference signs as FIG. 5, and description is omitted. Note that, in the description below, a case in which moving image information of captured training of joint movable range of a healthy person, and moving image information of captured training of joint movable range of a target person are obtained by obtaining circuitry 141, as moving image information to be displayed, will be described.

For example, when the moving image information of captured training of joint movable range of a healthy person, and the moving image information of captured training of joint movable range of a target person have been obtained by the obtaining circuitry 141, the identifying circuitry 142 extracts information that indicates a type of rehabilitation (training of joint movable range), from incidental information of the moving image information. Accordingly, the identifying circuitry 142 executes processing below.

Figure 9A:
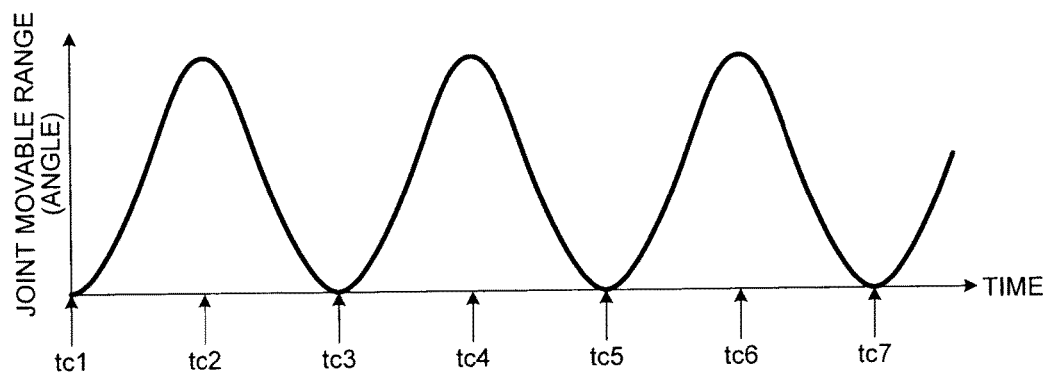
FIG. 9A is a diagram for describing processing of identifying circuitry according to a second embodiment.
Figure 9B:
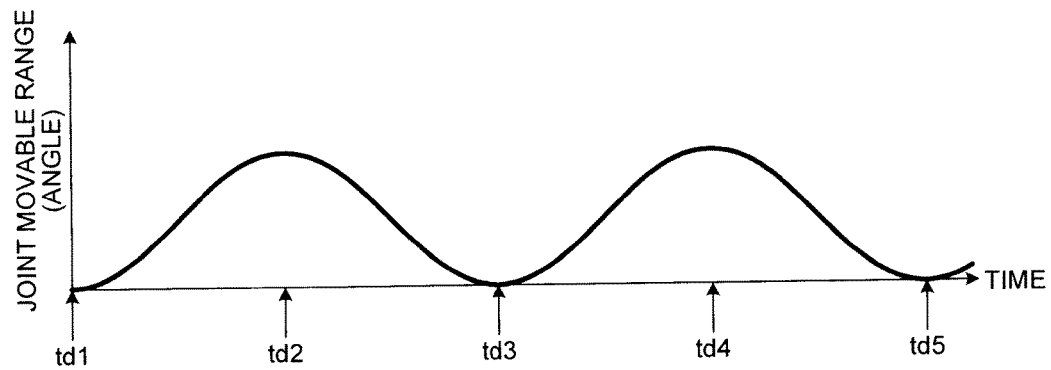
FIG. 9B is a diagram for describing the processing of the identifying circuitry according to the second embodiment.

FIGS. 9A and 9B are diagrams for describing processing of the identifying circuitry 142 according to the second embodiment. In FIGS. 9A and 9B, a case in which the identifying circuitry 142 identifies a timing at which the joint movable range is maximized, from a moving image of the training of joint movable range, will be described. Note that FIG. 9A is a graph illustrating change with time of the joint movable range of the healthy person, and FIG. 9B is a graph illustrating change with time of the joint movable range of the target person. In FIGS. 9A and 9B, the horizontal axes represent time, and vertical axes represent a value of the joint movable range. Note that this value is obtained such that the identifying circuitry 142 calculates the angle made by the front arm (from the joint $3f$ to the joint $3g$) before the movement and the front arm after the movement.

FIGS. 9A and 9B exemplarily illustrate the training of joint movable range from a reference position. That is, tc1 of FIG. 9A corresponds to a timing of a state in which the healthy person stretches the right arm straight (reference position). Further, tc2, tc4, and tc6 correspond to timings at which the joint movable range of the healthy person is maximized. Further, tc3, tc5, and tc7 correspond to timings at which the joint movable range of the healthy person is minimized. Further, td1 of FIG. 9B corresponds to a timing of a state in which the target person stretches the right arm straight (reference position). Further, td2 and td4 correspond to timings at which the joint movable range of the target person is maximized. Further, tc3 and tc5 correspond to timings at which the joint movable range of the target person is minimized. As illustrated in FIGS. 9A and 9B, the healthy person moves the right elbow at a higher pace than the target person, and the target person operates the right elbow at a slower pace than the healthy person. Note that, hereinafter, the timing at which the joint movable range is maximized may be abbreviated as "maximum timing". Further, for example, from tc2 to tc4 may be called "displacement period of an angle".

Here, a case in which improvement of a motion speed of the target person is specified as the purpose of rehabilitation will be described. In this case, the identifying circuitry 142 accepts an input for specifying the improvement of a motion speed of the target person, from the operator. When the improvement of a motion speed has been specified, the identifying circuitry 142 identifies a frame corresponding to the first maximum timing, from each frame group included in each of the moving image information obtained by the obtaining circuitry 141. To be specific, as illustrated in FIG. 9A, the identifying circuitry 142 refers to the motion information of the healthy person, and identifies the frame where a differential value of the joint movable range of the right elbow of the healthy person is changed from a positive value to a negative value. In the example illustrated in FIG. 9A, the identifying circuitry 142 identifies the frames respectively corresponding to tc2, tc4, and tc6, as the maximum timings of the healthy person. Then, the identifying circuitry 142 identifies the frame corresponding to tc2, which is the earliest time, of the identified frames respectively corresponding to tc2, tc4, and tc6, as the first maximum timing. Further, as illustrated in FIG. 9B, the identifying circuitry 142 identifies the frame corresponding to td2, as the first maximum timing of the target person, by similar processing.

Following that, the identifying circuitry 142 identifies the size of the subject captured in each of the moving image information (step S205). For example, the identifying circuitry 142 identifies a ratio occupied by the upper arm of the person to the number of pixels of a color image in the right and left direction, in the frame corresponding to the identified maximum timing, as the size of the subject. To be specific, the identifying circuitry 142 obtains coordinates of the right shoulder (joint $3e$) and the right elbow (joint $3f$) from the skeleton information of the frames respectively corresponding to tc2 and td2. The identifying circuitry 142 calculates pixel positions respectively corresponding to the obtained coordinates of the right shoulder and the right elbow. The identifying circuitry 142 calculates a ratio occupied by the number of pixels from the right shoulder to the right elbow to the number of pixels of the color image in the right and left direction, as the size of the subject. In this way, the identifying circuitry 142 identifies the size of the subject captured in each of the moving image information.

Further, a case in which improvement of a motion form of the target person is specified as the purpose of rehabilitation will be described. In this case, the identifying circuitry 142 accepts an input for specifying the improvement of a motion form of the target person, from the operator. When the improvement of a motion form has been specified, the identifying circuitry 142 identifies frames corresponding to all maximum timings, from each frame group included in each of the moving image information obtained by the obtaining circuitry 141. To be specific, as illustrated in FIG. 9A, the identifying circuitry 142 refers to the motion information of the healthy person, and identifies frames in which a differential value of the joint movable range of the right elbow of the healthy person is changed from a positive value to a negative value. In the example illustrated in FIG. 9A, the identifying circuitry 142 identifies frames respectively corresponding to tc2, tc4, and tc6, as the maximum timings of the healthy person. Further, as illustrated in FIG. 9B, the identifying circuitry 142 identifies frames respectively corresponding to td2 and td4, as all maximum timings of the target person, by similar processing.

Following that, the identifying circuitry 142 identifies the size of the subject captured in each of the moving image information. For example, the identifying circuitry 142 identifies a ratio occupied by the upper arm of the person to the number of pixels of the color image in the right and left direction, in the frame corresponding to the identified maximum timing, as the size of the subject. Here, when there is a plurality of the identified maximum timings, the identifying circuitry 142 identifies the size of the subject using the first maximum timing.

Note that the purpose of rehabilitation is not limited to the above-described example, and is appropriately set according to a type of the rehabilitation or a state of the target person. Then, processing for identifying an appropriate timing according to the set purpose is set to the identifying circuitry 142 in advance.

A case in which, regarding an effect of an operation, improvement of a motion form of the target person is specified before and after the operation will be described as an embodiment. In this case, the identifying circuitry 142 accepts an input for specifying the improvement of a motion form of the target person, from the operator. When the improvement of a motion form has been specified, the identifying circuitry 142 identifies frames corresponding to all maximum timings, from respective frame groups included in the moving image information before the operation and the moving image information after the operation.

For example, the display controlling circuitry 143 performs display control of the plurality of pieces of moving image information according to the purpose of rehabilitation. For example, when arranging and displaying a plurality of moving images of the training of joint movable range, the display controlling circuitry 143 performs the display control of the plurality of pieces of moving image information using the frames corresponding to the maximum timings identified by the identifying circuitry 142.

Figure 10:
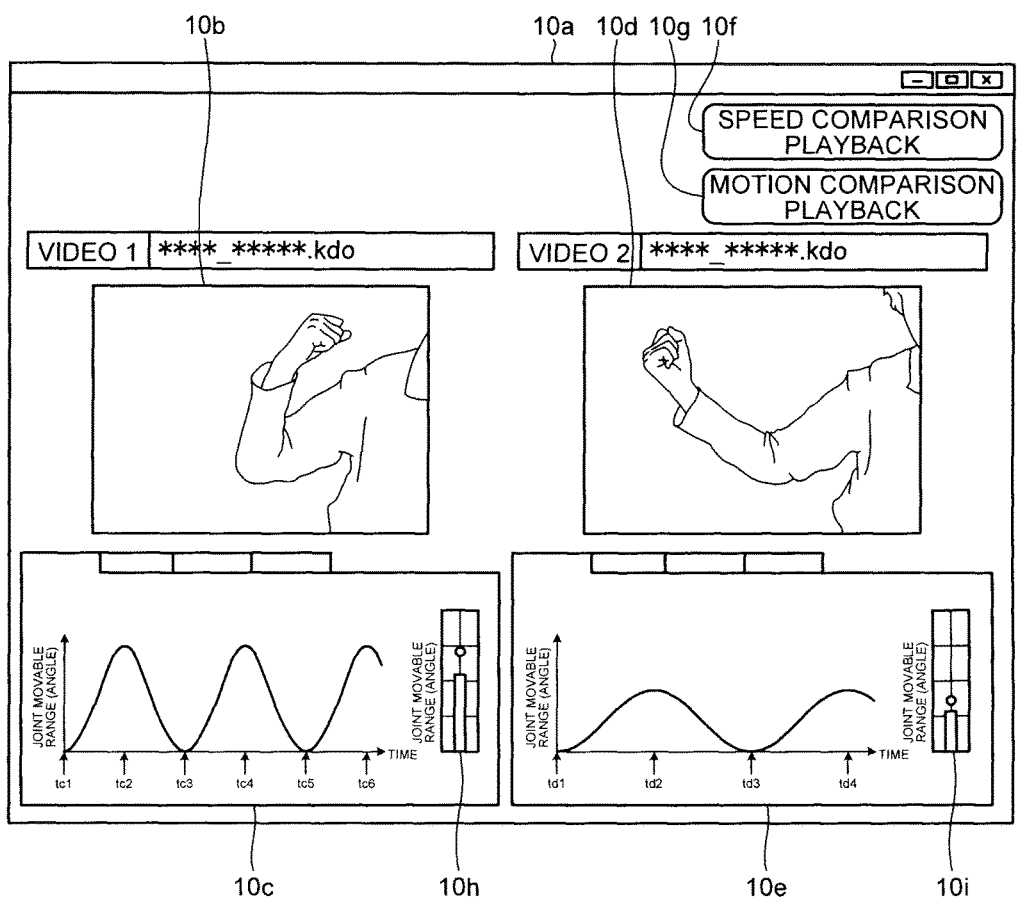
FIG. 10 is a diagram for describing processing of display controlling circuitry according to the second embodiment.

FIG. 10 is a diagram for describing processing of the display controlling circuitry 143 according to the second embodiment. FIG. 10 illustrates an example of a display screen 10a displayed by the display controlling circuitry 143. The display screen 10a includes a region 10b in which the moving image information of the healthy person is displayed, a region 10c where a graph indicating change with time of the joint movable range of the healthy person is displayed, a region 10d in which the moving image information of the target person is displayed, and a region 10e in which a graph indicating change with time of the joint movable range of the target person is displayed. Further, the display screen 10a includes a speed comparison playback button 10f for specifying improvement of a motion speed of the target person as the purpose of rehabilitation, and a motion comparison playback button 10g for specifying the improvement of a motion form of the target person. Further, the display screen 10a includes graphs 10h and 10i that display a bar of a current value (an angle of a currently displayed frame in the case of moving image playback) and a point indicating a maximum value (a maximum value of angles up to the currently displayed frame in the case of moving image playback), in the training of joint movable range.

Here, an example in which the improvement of a motion speed of the target person is specified as the purpose of rehabilitation will be described. For example, the identifying circuitry 142 accepts information that indicates that the speed comparison playback button 10f has been pressed by the operator, from an input circuitry 120. Then, the display controlling circuitry 143 performs playback control so as to cause the sizes of the target person and start timings of the moving image information to accord with each other. To be specific, the display controlling circuitry 143 enlarges or reduces the moving image information of the healthy person and the moving image information of the target person such that the upper arms of the healthy person and the target person can be nearly the same size, using the sizes of the subjects identified by the identifying circuitry 142. Following that, the display controlling circuitry 143 plays back these two pieces of moving image information at the same time such that the moving image information of the healthy person is started from the frame corresponding to tc2, and the moving image information of the target person is started from the frame corresponding to td2.

Further, a case in which an effect of an operation is confirmed by how much a movable speed (motion speed) of the target person is improved before and after the operation will be described. In this case, for example, the identifying circuitry 142 accepts information that indicates that the speed comparison playback button 10f has been pressed by the operator, from the input circuitry 120. Then, the display controlling circuitry 143 performs the playback control so as to cause the sizes of the target person and start timings of the moving image information before the operation and the moving image information after the operation to accord with each other. Note that the above-described example is a mere example, and there is a case in which the effect of an operation before and after the operation is confirmed by how much the movable range (angle) is improved, for example.

Further, a case in which improvement of a motion form of the target person is specified as the purpose of rehabilitation will be described. For example, the identifying circuitry 142 accepts information that indicates that the motion comparison playback button 10g has been pressed by the operator, from the input circuitry 120. Then, the display controlling circuitry 143 performs the playback control so as to cause the sizes of the target person and the maximum timings of the moving image information to accord with each other. To be specific, the display controlling circuitry 143 enlarges or reduces the moving image information of the healthy person and the moving image information of the target person such that the upper arms of the healthy person and the target person can have nearly the same size, using the sizes of the subjects identified by the identifying circuitry 142. Following that, the display controlling circuitry 143 synchronizes the maximum timings of the healthy person with the maximum timings of the target person, and plays back the moving image information. To be specific, since the number of frames from td1 to td2 is larger than the number of frames from tc1 to tc2, the display controlling circuitry 143 partially thins out the frames from td1 to td2. Accordingly, the display controlling circuitry 143 plays back the moving image information so as to display the frames corresponding to tc2 and td2 at the same time. Further, since the number of frames from td2 to td4 is larger than the number of frames from tc2 to tc4, the display controlling circuitry 143 partially thins out the frames from td2 to td4. Accordingly, the display controlling circuitry 143 plays back the moving image information so as to display the frames corresponding to tc4 and td4 at the same time. In this way, the display controlling circuitry 143 plays back the moving image information so as to cause the maximum timings to accord with each other.

Figure 11:
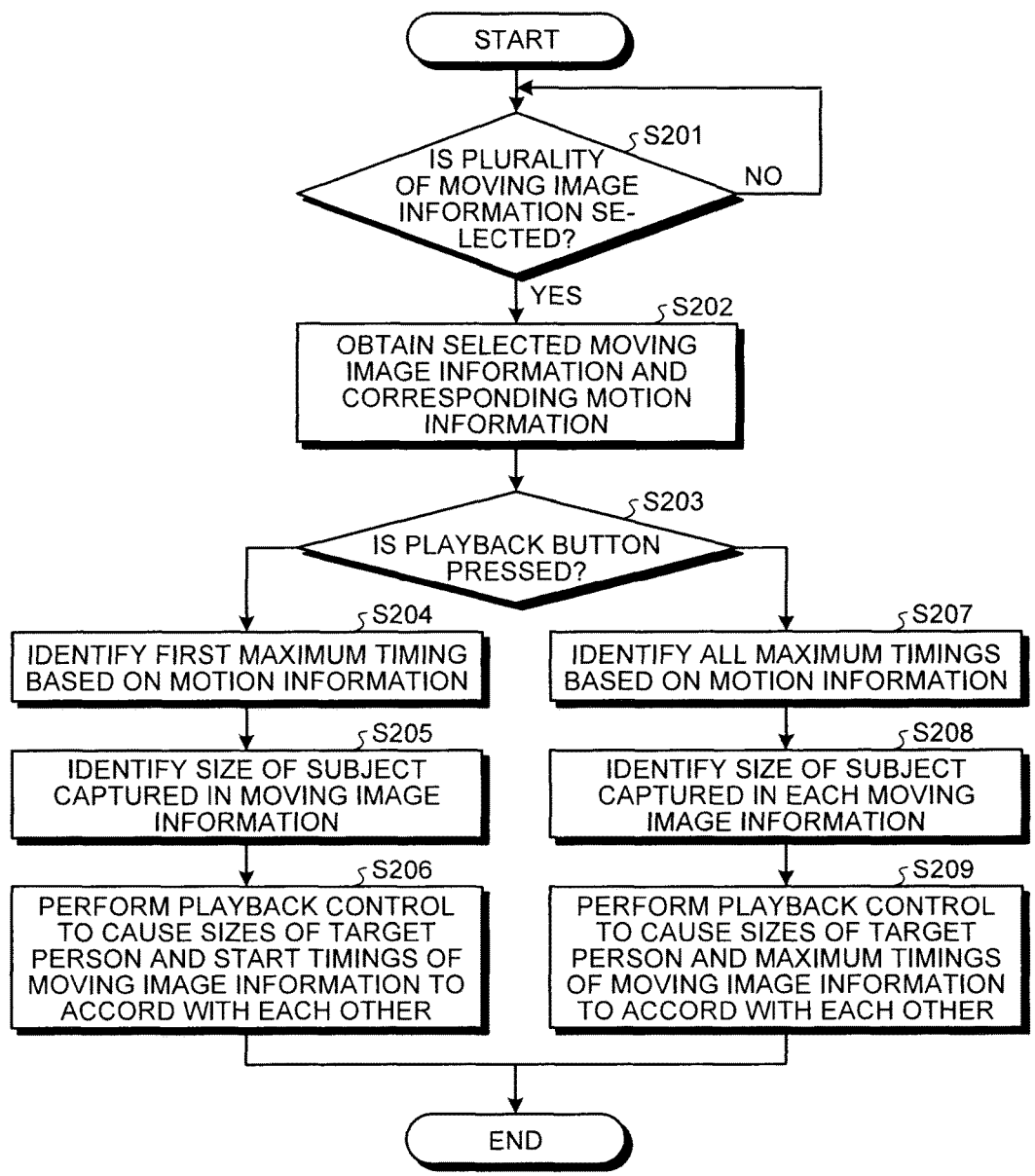
FIG. 11 is a flowchart for describing an example of a processing procedure of a motion information display apparatus according to the second embodiment.

Next, a processing procedure of the motion information display apparatus 100 according to the second embodiment will be described with reference to FIG. 11. FIG. 11 is a flowchart for describing an example of a processing procedure of the motion information display apparatus 100 according to the second embodiment.

As illustrated in FIG. 11, when a plurality of pieces of moving image information has been selected (Yes at step S201), the obtaining circuitry 141 obtains the selected pieces of moving image information, and corresponding motion information (step S202). Note that the obtaining circuitry 141 is in a stand-by state until the plurality of pieces of moving image information is selected (No at step S201).

Following that, the identifying circuitry 142 accepts the information that indicates that the playback button has been pressed (step S203). When the speed comparison playback button has been pressed at step S203, the identifying circuitry 142 identifies a frame corresponding to the maximum timing of a certain point of time, based on each of the motion information obtained in the obtaining circuitry 141 (step S204). Following that, the identifying circuitry 142 identifies the size of the subject captured in each of the moving image information (step S205). Then, the display controlling circuitry 143 performs the playback control so as to cause the sizes of the target person and the start timings of the moving image information to accord with each other (step S206), and terminates the processing.

Further, when the motion comparison playback button has been pressed at step S203, the identifying circuitry 142 identifies frames corresponding to all maximum timings, based on each of the motion information obtained by the obtaining circuitry 141 (step S207). Following that the identifying circuitry 142 identifies the size of the subject captured in each of the moving image information (step S208). Then, the display controlling circuitry 143 performs the playback control so as to cause the sizes of the target person and the maximum timings of the moving image information to accord with each other (step S209), and terminates the processing.

As described above, the motion information display apparatus 100 according to the second embodiment can be applied to the case where a moving image of another training is displayed, for example, the case where a moving image of the training of joint movable range is displayed.

Third Embodiment

The first and second embodiments have been described so far. However, various types of different embodiments may be implemented, other than the first and second embodiments.

(Superimposition Display of Moving Image Information and Motion Information)

For example, in the first and second embodiments, the cases where two or more pieces of moving image information are arranged and played back have been described. However, an embodiment is not limited to the cases. For example, motion information may be superimposed and displayed on the played-back moving image information.

Figure 12A:
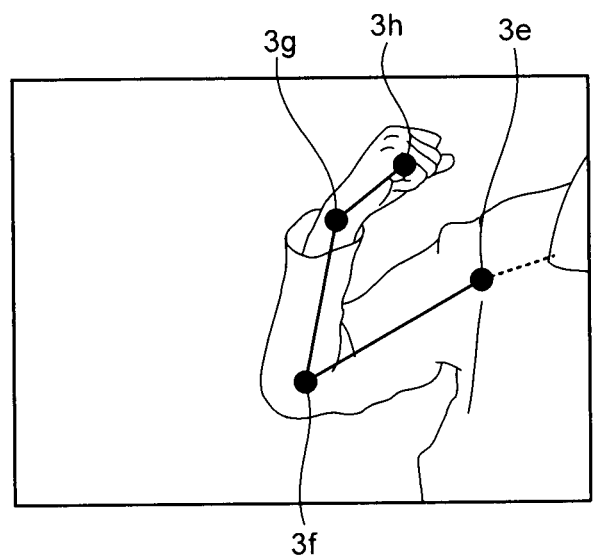
FIG. 12A is a diagram for describing superimposition display of moving image information and motion information.
Figure 12B:
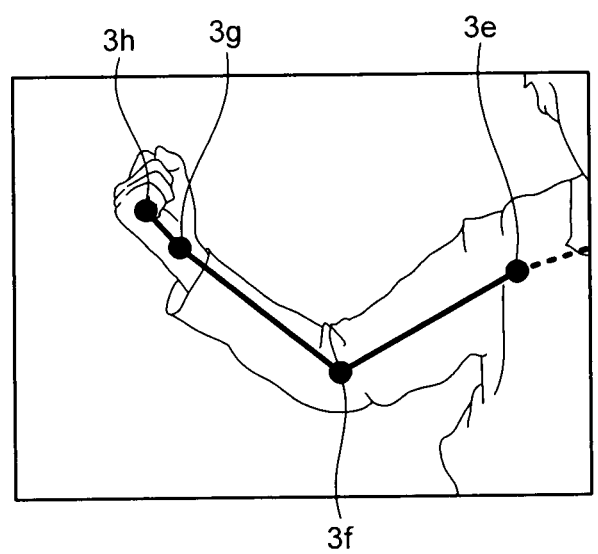
FIG. 12B is a diagram for describing the superimposition display of the moving image information and the motion information.

FIGS. 12A and 12B are diagrams for describing superimposition display of moving image information and motion information. FIG. 12A exemplarily illustrates a display image in which corresponding motion information is superimposed and displayed on moving image information of training of joint movable range of a healthy person. Further, FIG. 12B exemplarily illustrates a display image in which corresponding motion information is superimposed and displayed on moving image information of training of joint movable range of a target person.

As illustrated in FIGS. 12A and 12B, a display controlling circuitry 143 superimposes and displays, on moving image information to be displayed, skeleton information corresponding to frames included in the moving image information. To be specific, when displaying a moving image of the training of joint movable range of a right arm, the display controlling circuitry 143 generates a display image in which information that indicates positions of a right shoulder (a joint 3e), a right elbow (a joint 3f), a right wrist (a joint 3g), and a right hand (a joint 3h) to be displayed are superimposed on a color image. Then, the display controlling circuitry 143 performs display control of the generated display image using a frame corresponding to a maximum timing identified by identifying circuitry 142. In this way, the motion information display apparatus 100 can clearly indicate the magnitude of the joint movable range by superimposing and displaying the motion information on the played-back moving image information.

(Synchronization Playback of Motion Information)

Further, for example, in an embodiment, not only the superimposition display, but also synchronization play back may be performed using only the motion information corresponding to the moving image information, as a moving image. To be specific, the display controlling circuitry 143 synchronizes and displays, in place of the color image of the moving image information to be displayed, the skeleton information corresponding to frames included in the moving image information, as a moving image.

Figure 13A:
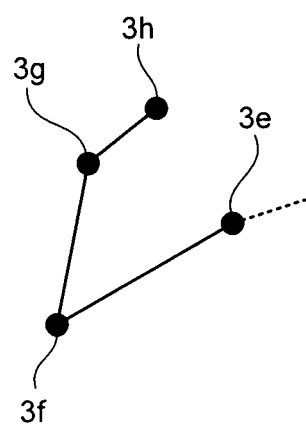
FIG. 13A is a diagram for describing synchronization playback of the motion information.
Figure 13B:
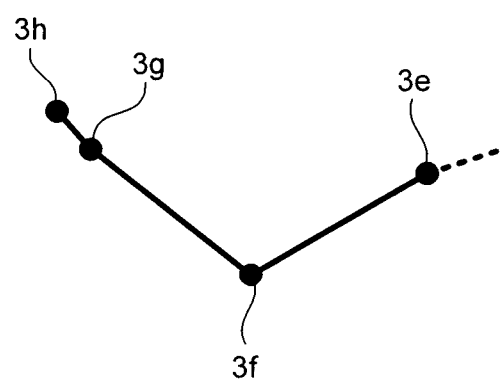
FIG. 13B is a diagram for describing the synchronization playback of the motion information.

FIGS. 13A and 13B are diagrams for describing the synchronization playback of the motion information. FIG. 13A exemplarily illustrates a display image that displays the motion information of the training of joint movable range of the healthy person, as a moving image. Further, FIG. 13B exemplarily illustrates a display image that displays the motion information of the training of joint movable range of the target person, as a moving image.

As illustrated in FIGS. 13A and 13B, the display controlling circuitry 143 generates display images that display the skeleton information corresponding to frames of the moving information respectively corresponding to the moving image information of the healthy person and the moving image information of the target person, as moving images. To be specific, when displaying the moving images of the training of joint movable range of the right arm, the display controlling circuitry 143 generates the display images that display information indicating positions of right shoulders (joints 3e), right elbows (joints 3f), right wrists (joints 3g), and right hand (joints 3h) to be displayed. Then, the display controlling circuitry 143 performs display control of the generated display images, using the frames corresponding to maximum timings identified by the identifying circuitry 142. In this way, the motion information display apparatus 100 can clearly indicate the magnitude of the joint movable range by displaying only the motion information. Further, for example, the display controlling circuitry 143 may display the joints, which are portions to be focused, in a different color from others.

(Adjustment of Direction of Subject)

Further, for example, in the first and second embodiments, the cases of displaying the moving images without causing directions of the subjects to accord with each other have been described. However, it may be possible to display the moving images after the directions of the subjects are caused to accord with each other. For example, the display controlling circuitry 143 performs display control after translating and rotating at least one piece of the moving image information so as to cause the directions of the subjects to approximately accord with each other between the moving image information.

FIGS. 13A and 13B are diagrams for describing adjustment of directions of subjects. FIG. 13A exemplarily illustrates a display image that displays the motion information of the training of joint movable range of the healthy person. Further, FIG. 13B exemplarily illustrates a display image that displays the motion information of the training of joint movable range of the target person.

As illustrated in FIGS. 13A and 13B, the display controlling circuitry 143 displays the skeleton information corresponding to frames included in the motion information corresponding to the moving image information, in place of the moving image information to be displayed, as moving images, after adjusting the directions of the subjects. To be specific, when displaying moving images of the training of joint movable range of the right arm, the display controlling circuitry 143 extracts the information that indicates positions of right shoulders (joints 3*e*), right elbows (joints 3*f*), right wrists (joints 3*g*), and right hands (joints 3*h*) to be displayed, from the skeleton information of the healthy person and the target person. Following that, the display controlling circuitry 143 translates the motion information of the target person (calculates the coordinates) such that the position of the right elbow of the target person accord with the position of the right elbow of the healthy person. Following that, the display controlling circuitry 143 rotates the motion information of the target person around the position of the right elbow (calculates the coordinated) such that the upper arm of the target person is superimposed on the upper arm of the healthy person. Following that, the display controlling circuitry 143 rotates the motion information of the target person using the position of the upper arm as a rotation axis (calculates the coordinates) such that the direction into which the target person moves the front arm accord with the direction into which the healthy person moves the front arm. Then, the display controlling circuitry 143 synchronizes and displays the motion information of the healthy person and the motion information of the target person, in the translated and rotated direction. In this way, the motion information display apparatus 100 can display the moving images after adjusting the directions of the subjects. Note that a method of adjusting the directions of the subjects is not limited to the above-described example, and three-dimensional conversion or the like may be used, for example.

(Superimposition Display of Plurality of Moving Images)

Further, for example, in the first and second embodiments, the cases of arranging and displaying the moving images to be displayed have been described. However, an embodiment is not limited to the cases. For example, moving images to be displayed may be superimposed and displayed.

Figure 14:
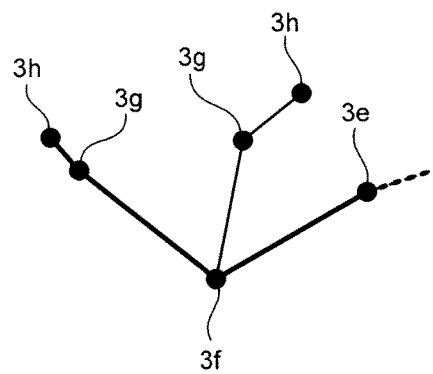
FIG. 14 is a diagram for describing superimposition display.

FIG. 14 is a diagram for describing superimposition display. FIG. 14 exemplarily illustrates a display image in which the motion information of the training of joint movable range of the healthy person, and the motion information of the training of joint movable range of the target person are superimposed and displayed.

As illustrated in FIG. 14, the display controlling circuitry 143 superimposes and displays the skeleton information corresponding to frames included in the motion information to be displayed. To be specific, when displaying moving images of the training of joint movable range of the right arm, the display controlling circuitry 143 extracts the information that indicates positions of right shoulders (joints 3*e*), right elbows (joints 3*f*), right wrists (joints 3*g*), and right hands (joints 3*h*) to be displayed, from the skeleton information of the healthy person and the target person. Then, the display controlling circuitry 143 generates a superimposition image such that the positions of the right shoulder and the right elbow of the healthy person, and the positions of the right shoulder and the right elbow of the target person accord with each other, respectively. Then, the display controlling circuitry 143 displays the generated superimposition image in output circuitry 110. In this way, the motion information display apparatus 100 can superimpose and display a plurality of moving images. At this time, types of lines or colors can be changed and displayed so that whether it is the motion information of the healthy person or the motion information of the target person can be distinguished.

(Synchronization Playback of Other Moving Images (Footprint Moving Images))

Further, moving images synchronized and played back by the motion information display apparatus 100 are not limited to the above-described color image information and skeleton information. The motion information display apparatus 100 may synchronizes and plays back other moving images based on the motion information. For example, the motion information display apparatus 100 may synchronizes and plays back footprint moving images. The footprint moving image is an image that sequentially displays landing positions where both feet of a person land on the floor surface when the person walks, for example.

Figure 15:
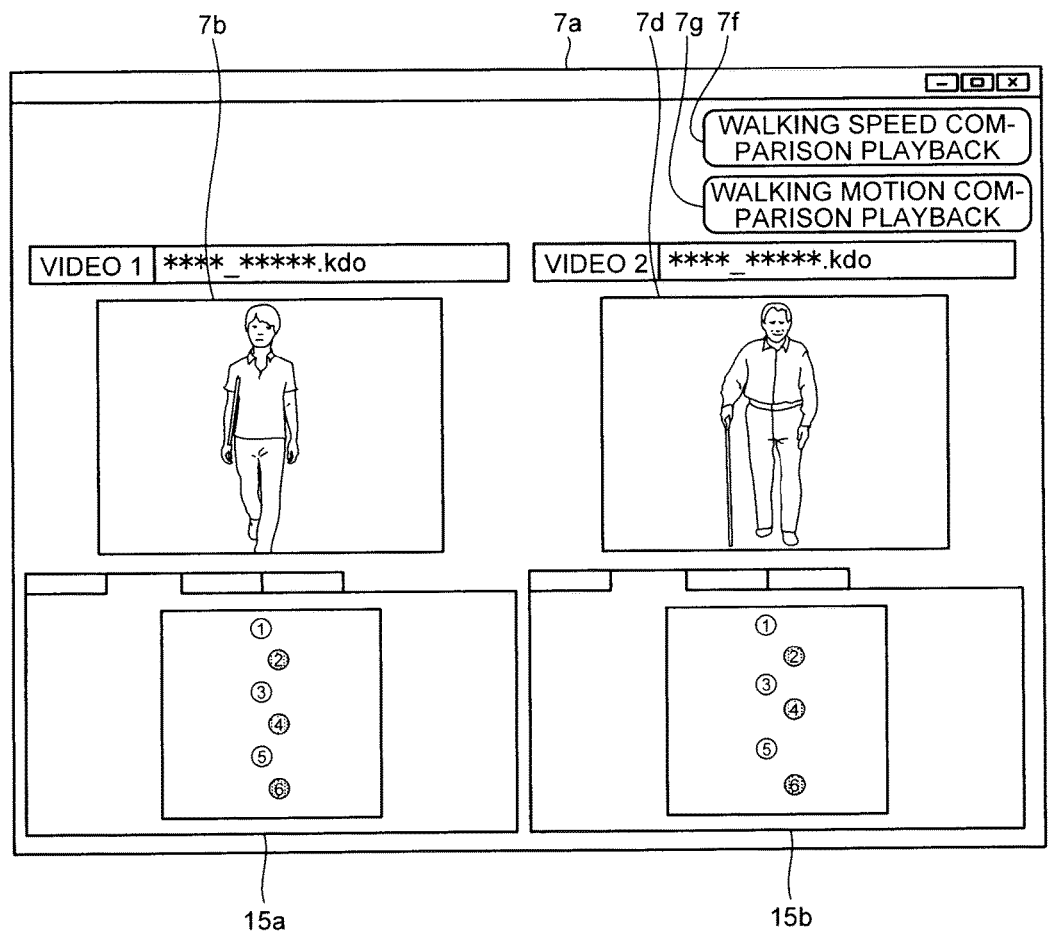
FIG. 15 is a diagram for describing synchronization playback of a footprint moving image.

FIG. 15 is a diagram for describing synchronization playback of the footprint moving images. FIG. 15 illustrates an example of a display screen 7*a* displayed in the output circuitry 110 by the display controlling circuitry 143. The display screen 7*a* is different from the display screen 7*a* exemplarily illustrated in FIG. 7, in that a region 15*a* is included in place of the region 7*c*, and a region 15*b* is included in place of the region 7*e*. In the region 15*a*, the footprint moving image of the healthy person who is displayed in the moving image in the region 7*b* is displayed, and in the region 15*b*, the footprint moving image of the target person who is displayed in the moving image in the region 7*d* is displayed.

In the regions 15*a* and 15*b*, the horizontal direction corresponds to an x axis direction of a world coordinate system, and the vertical direction corresponds to a z axis direction of the world coordinate system. That is, the regions 15*a* and 15*b* correspond to diagrams of a floor surface where a person walks, as viewed from above. Further, in the region 15*a*, the circles with numbers on non-colored background correspond to the landing positions (coordinates) of the right foot of the person, the circles with numbers on colored background correspond to the landing positions (coordinates) of the left foot of the person, and the numbers in the circles indicate what number landing positions. This footprint moving image is generated by the display controlling circuitry 143, for example.

Here, processing of generating the footprint moving image by the display controlling circuitry 143 will be described. For example, the display controlling circuitry 143 generates the footprint moving image using landing timings identified by the identifying circuitry 142. To be specific, the display controlling circuitry 143 obtains the coordinates of the tarsi of the landed feet (the joint 3p or the joint 3t), respectively, from frames corresponding to the landing timings of the both feet identified by the identifying circuitry 142. Then, the display controlling circuitry 143 generates a moving image that displays xz coordinates of the obtained respective tarsi on the floor surface, in the frames corresponding to the landing timings of the feet of the person. In the example illustrated in FIG. 15, the display controlling circuitry 143 generates a moving image that displays the circle with "1" on non-colored background at the first landing timing of the right foot, the circle with "2" on colored background at the first landing timing of the left foot, the circle with "3" on non-colored background at the second landing timing of the right foot, the circle with "4" on colored background at the second landing timing of the left foot, the circle with "5" on non-colored background at the third landing timing of the right foot, and the circle with "6" on colored background at the third landing timing of the left foot. In this way, the display controlling circuitry 143 generates the footprint moving images respectively displayed in the regions 15a and 15b.

As illustrated in FIG. 15, the display controlling circuitry 143 performs display control of the footprint moving images respectively displayed in the regions 15a and 15b using the frames corresponding to the landing timings identified by the identifying circuitry 142. For example, when comparing walking speeds, the display controlling circuitry 143 plays back these two footprint moving images at the same time such that the first landing timings of the right feet displayed in the regions 15a and 15b accord with each other. In this way, the motion information display apparatus 100 can perform playback control of a plurality of footprint moving images.

(Synchronization Playback of Other Moving Images (Graph Moving Images))

Further, for example, the motion information display apparatus 100 may synchronize and play back graph moving images, as other moving images based on the motion information. The graph moving image is a graph that illustrates information related to movement of a position of a target position, and is a moving image that plots a graph with elapsed time, the graph illustrating a predetermined value that is changed with a motion of a person. In other words, the graph moving image is a moving image that displays a graph as if to draw a certain graph. Note that, as the predetermined value, a value that can be calculated from the skeleton information, such as a walking speed of each frame or an angle of a knee joint of each frame, is arbitrarily selected by an operator.

Figure 16:
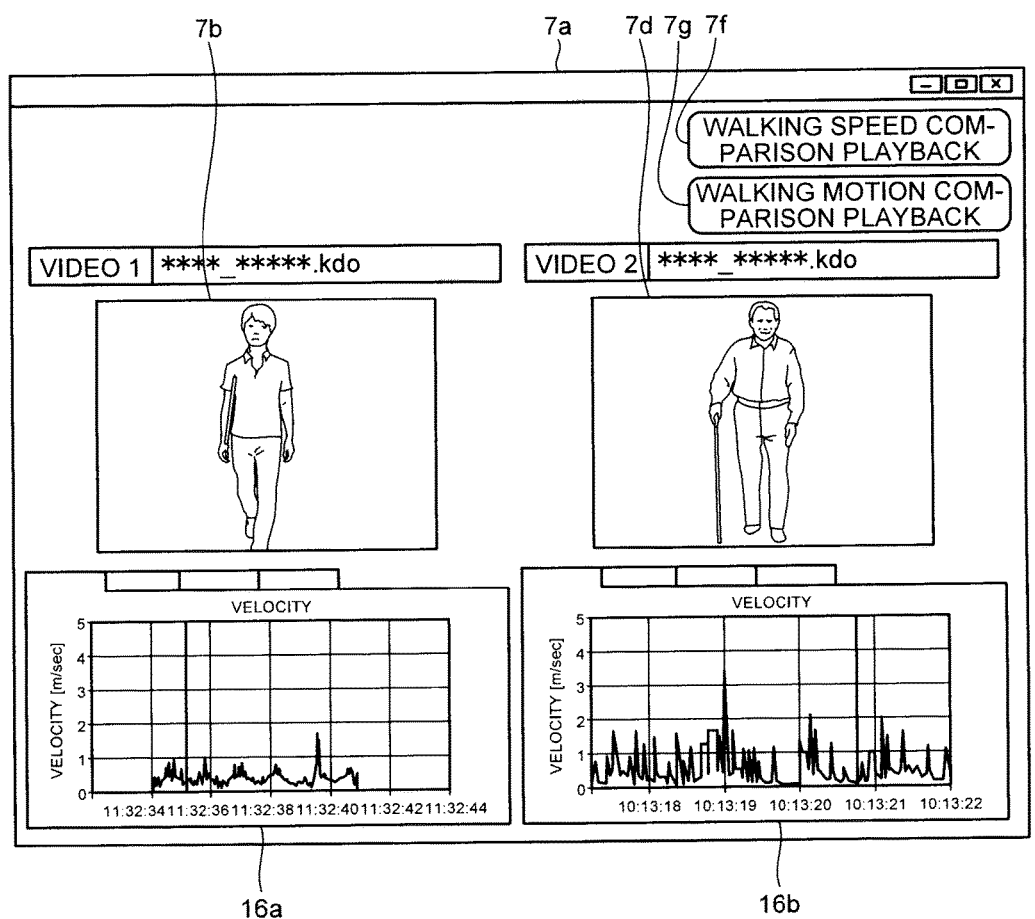
FIG. 16 is a diagram for describing synchronization playback of a graph moving image.

FIG. 16 is a diagram for describing the synchronization playback of the graph moving images. FIG. 16 illustrates an example of a display screen 7a displayed in the output circuitry 110 by the display controlling circuitry 143. The display screen 7a is different from the display screen 7a exemplarily illustrated in FIG. 7, in that a region 16a is included in place of the region 7c, and a region 16b is included in place of the region 7e. In the region 16a, the graph moving image that illustrates the walking speed of the healthy person who is displayed in the moving image in the region 7b is displayed, and in the region 15b, the graph moving image that displays the walking speed of the target person who is displayed in the moving image in the region 7d is displayed.

In the regions 16a and 16b, the horizontal direction corresponds to time, and the vertical direction corresponds to velocity (the walking speed). These footprint moving images are generated by the display controlling circuitry 143, for example. To be specific, the display controlling circuitry 143 calculates moving distances per unit time of the waists (joints 3c) of respective persons displayed in the regions 7b and 7d, for each frame, as the walking speeds. Then, the display controlling circuitry 143 generates the graph moving images that plot the calculated walking speeds of each frame, with elapsed time.

As illustrated in FIG. 16, the display controlling circuitry 143 performs the display control of the graph moving images respectively displayed in the regions 16a and 16b using the frames corresponding to the landing timings identified by the identifying circuitry 142. For example, when comparing the walking speeds, the display controlling circuitry 143 plays back these two footprint moving images at the same time such that the first landing timings of the right feet displayed in the regions 16a and 16b accord with each other. In this way, the motion information display apparatus 100 can perform playback control of a plurality of graph moving images. Note that the graph moving images that the motion information display apparatus 100 performs the playback control is not limited to the above-described example. For example, the motion information display apparatus 100 may perform the playback control of an arbitrary graph with values on the vertical axis, the values being able to be calculated from the skeleton information. To be specific, the motion information display apparatus 100 may perform the playback control of the graphs 10h and 10i exemplarily illustrated in FIG. 10.

Note that, in the example of FIG. 16, the horizontal direction is time, and the vertical direction is a speed. However, an embodiment is not limited to the example. For example, when the horizontal direction is time, the vertical direction may be a position (coordinates), or may be acceleration. That is, an embodiment may be applied to a graph that illustrates an arbitrary parameter that can be calculated from the motion information.

(Synchronization Playback of Other Moving Images (Moving Images Accompanying Highlighting))

Further, for example, the motion information display apparatus 100 may synchronize and play back moving images accompanying highlighting of the display screen 7a illustrated in FIG. 7. As an example, the display controlling circuitry 143 further displays information related to playback control, of moving images based on the motion information.

Figure 17:
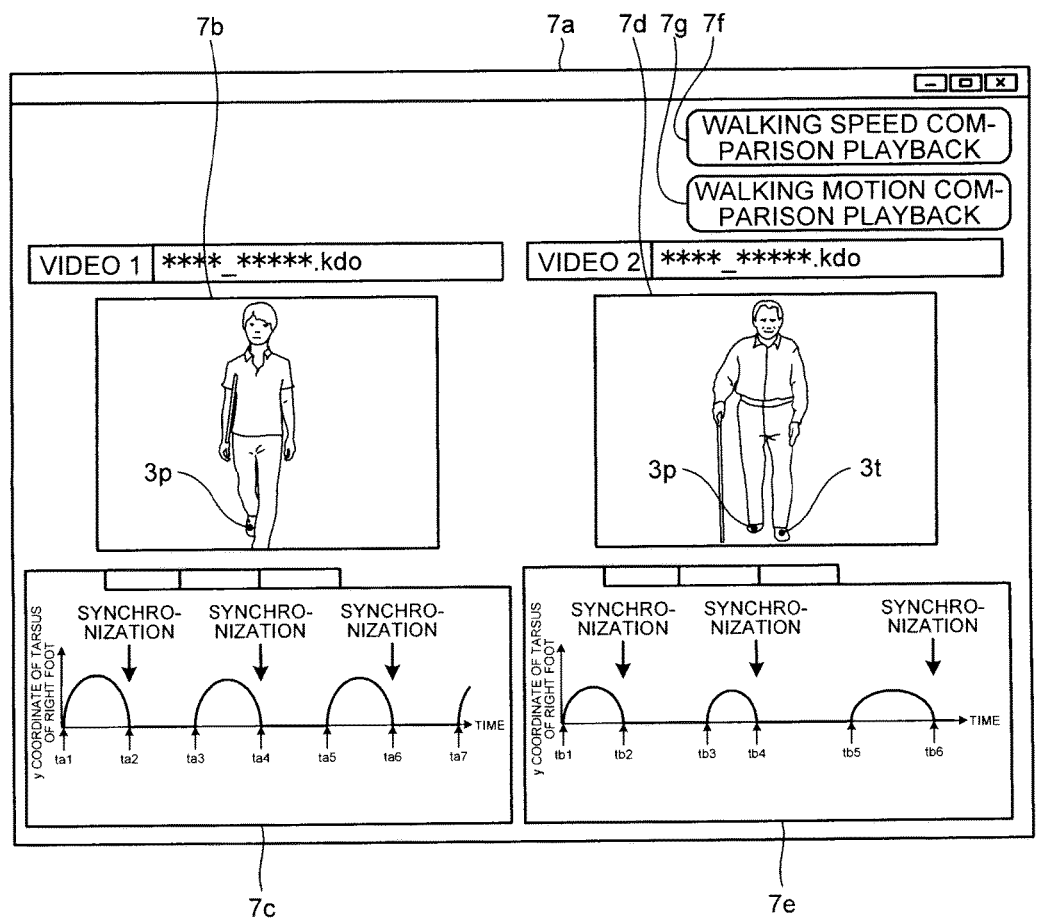
FIG. 17 is a diagram for describing synchronization playback of a moving image accompanying highlighting.

FIG. 17 is a diagram for describing synchronization playback of moving images accompanying highlighting. FIG. 17 illustrates an example of a display screen 7a displayed in the output circuitry 110 by the display controlling circuitry 143. This display screen 7a is different from the display screen 7a exemplarily illustrated in FIG. 7, in that the joints 3p and 3t are included in the regions 7b and 7d, and arrows that indicate timings corresponding to frame used for synchronization (playback control) are included.

For example, the display controlling circuitry 143 highlights and displays points that indicate the joints 3p and 3t, which serve as focused portions in walking training, in the regions 7b and 7d. Further, for example, the display controlling circuitry 143 highlights and displays the arrows (the arrows with "synchronization" in the drawing) that point out the timings of ta2, ta4, ta6, tb2, tb4, and tb6, which are frames used for synchronization, in regions 7c and 7e.

As illustrated in FIG. 17, the display controlling circuitry 143 performs display control of moving images accompanying highlighting, using frames corresponding to landing timings identified by the identifying circuitry 142. Note that, the display controlling circuitry 143 may perform characteristic display for illustrating a timing corresponding to a frame identified by the identifying circuitry 142.

(Application to Service Providing Apparatus)

In the first and second embodiments, the cases in which the motion information display apparatus 100 performs comparison display have been described. However, an embodiment is not limited to the cases, and for example, processing may be executed by a service providing apparatus on a network.

Figure 18:
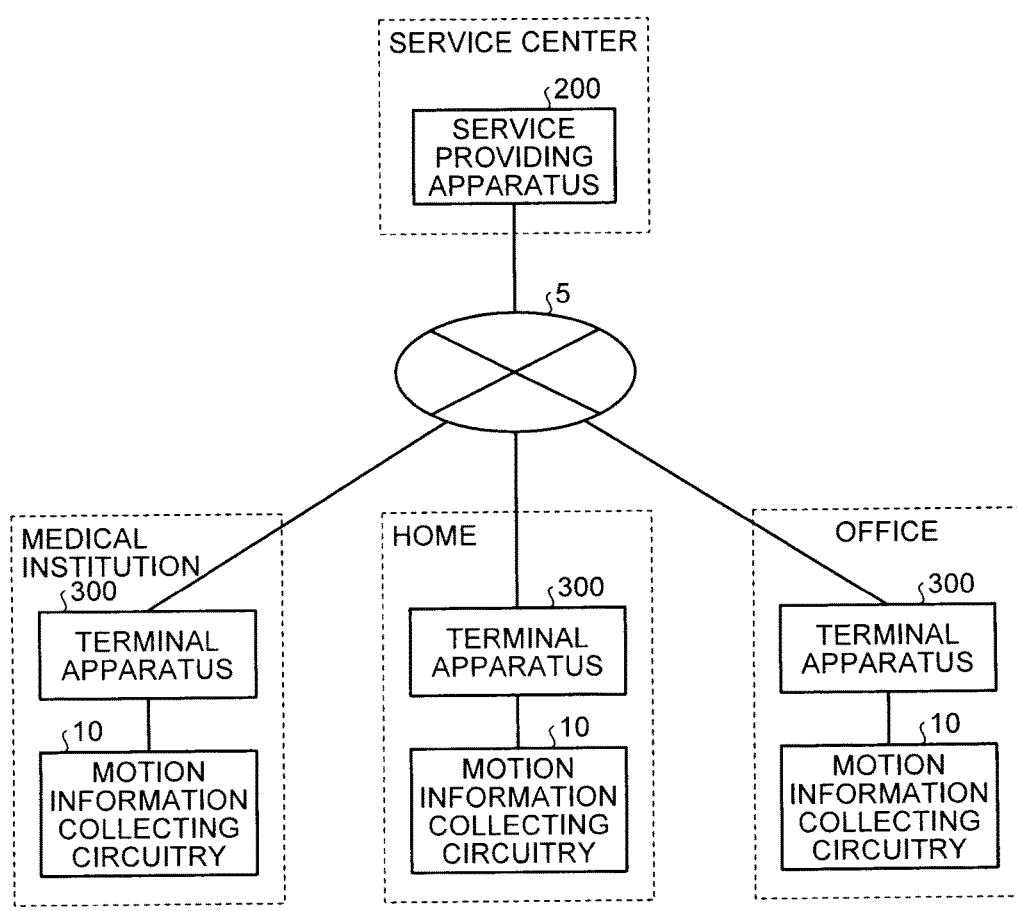
FIG. 18 is a diagram for describing an example applied to a service providing apparatus.

FIG. 18 is a diagram for describing an example applied to a service providing apparatus. As illustrated in FIG. 18, a service providing apparatus 200 is arranged in a service center, and is connected with terminal apparatuses 300 arranged in a medical institution, a home, and an office, respectively, through a network 5, for example. Respective motion information collecting circuitry 10 are connected to the terminal apparatuses 300 arranged in the medical institution, the home, and the office, respectively. Further, each of the terminal apparatuses 300 includes a client function that uses a service provided by the service providing apparatus 200. Further, as the network 5, any type of communication network regardless of wired or wireless, such as the Internet or a wide area network (WAN), can be employed.

For example, the service providing apparatus 200 has a similar function to the motion information display apparatus 100 described in FIG. 5, and provides the function to the terminal apparatus 300, as a service. In this case, the terminal apparatus 300 uploads, to the service providing apparatus 200, motion information and moving image information collected by the motion information collecting circuitry 10 in the medical institution, the home, or the office where rehabilitation is performed. The service providing apparatus 200 stores the motion information and the moving image information uploaded by the terminal apparatus 300.

Here, the service providing apparatus 200 has function circuitry respectively similar to the obtaining circuitry 141, the identifying circuitry 142, and the display controlling circuitry 143. Then, the function circuitry similar to the obtaining circuitry 141 obtains a plurality of pieces of the moving image information, and the motion information that indicates a motion of a subject included in each of the moving image information. Then, the function circuitry similar to the identifying circuitry 142 identifies a frame corresponding to a timing of a predetermined motion performed in the rehabilitation, from each frame group included in each of the moving image information, based on the motion information. Then, the function circuitry similar to the display controlling circuitry 143 performs display control of the plurality of the pieces of the moving image information using the frame corresponding to a timing of a predetermined motion.

To be specific, an operator specifies a plurality of pieces of the moving image information to be displayed, using the terminal apparatus 300. The terminal apparatus 300 transmits information that indicates the specified plurality of pieces of the moving image information to the service providing apparatus 200. The service providing apparatus 200 generates a display image for comparing and displaying the specified plurality of pieces of the moving image information by the above-described function, and transmits the display image to the terminal apparatus 300. Accordingly, the operator can view the display image that displays and compares the specified plurality of pieces of the moving image information, on the terminal apparatus 300.

Note that the service providing apparatus 200 may have a configuration to perform a service of storing the motion information and the moving image information only. In this case, the terminal apparatus 300 has a function similar to the motion information display apparatus 100 described in FIG. 5. Then, the terminal apparatus 300 appropriately downloads the moving image information and the motion information to be displayed, from the service providing apparatus 200, and performs the above-described display control by functions respectively similar to the obtaining circuitry 141, the identifying circuitry 142, and the display controlling circuitry 143.

OTHER EMBODIMENTS

The configuration of the motion information display apparatus 100 in the above-described embodiments is a mere example, and integration and separation of the circuitry can be appropriately performed.

For example, in the above-described embodiments, the cases applied to the walking training and the training of joint movable range have been described. However, an embodiment is not limited to the cases, and can be applied to muscle build-up training of kinesitherapy, physiotherapy, or electrotherapy, for example.

Further, for example, the configuration of the motion information display apparatus 100 in the embodiments may be included in any apparatus in the medical-use information system. For example, a motion information processing apparatus 20 may include a configuration of a motion information display apparatus 100.

Further, for example, in the above-described embodiments, the cases where the sizes of the subjects included in the moving image information are caused to accord with each other have been described. However, an embodiment is not limited to the cases, and the processing to cause the sizes of the subjects to accord with each other may not be executed.

Further, for example, in the above-described embodiments, the cases in which the moving image information or the motion information is displayed have been described. However, an embodiment is not limited to the cases. That is, the processing to display the moving image information or the motion information may not be executed. For example, a motion information display apparatus 100 may identify a frame corresponding to a timing of a predetermined motion performed in rehabilitation, and further causes moving image information to accompany information that indicates the identified frame, or display the information that indicates the identified frame in a graph or the like. When causing the moving image information to accompany the information that indicates the identified frame, for example, a apparatus different from a motion information display apparatus 100 may obtain the moving image information and incidental information, and perform display control like the above-described embodiments, according to the incidental information.

Further, for example, in the above-described embodiments, the cases where the moving image information stored in the medical-use image storage apparatus 40 is displayed and compared have been described. However, an embodiment is not limited to the cases. For example, a motion information display apparatus 100 may display and compare moving image information acquired from a motion information processing apparatus 20 in approximately real time, and moving image information stored in a medical-use image storage apparatus 40. According to this configuration, the motion information display apparatus 100 can synchronize timing of the moving image information stored in the past and a motion about a target person, and display and compare the information and the motion, while capturing a moving image of rehabilitation of the target person.

Further, the functions of the obtaining circuitry 141, the identifying circuitry 142, and the display controlling circuitry 143 described in the above-described embodiments can be realized by software. For example, a computer executes a motion information display program that defines the procedure of the processing, which has been described being performed by the obtaining circuitry 141, the identifying circuitry 142, and the display controlling circuitry 143 in the above-described embodiments, so that the functions of the obtaining circuitry 141, the identifying circuitry 142, and the display controlling circuitry 143 are realized. This motion information display program is stored in a hard disk or a semiconductor memory element, for example, and is read and executed by a processor such as a CPU or a micro-processing circuitry (MPU). Further, this medical-use image display program can be recorded on a computer-readable recording medium such as a compact disc-read only memory (CD-ROM), a magnetic optical disk (MO), or a digital versatile disk (DVD), and can be distributed.

Note that not only the rule information of rehabilitation, recommended helping state, and the like defined by Japanese Orthopaedic Association according to the first to third embodiments, but also rules and regulations defined by other various organizations may be used. For example, various rules and regulations defined by "International Society of Orthopaedic Surgery and Traumatology (SICOT)", "American Academy of Orthopaedic Surgeons (AAOS)", "European Orthopaedic Research Society (EORS)", "International Society of Physical and Rehabilitation Medicine (ISPRM)", "American Academy of Physical Medicine and Rehabilitation (AAPM & R)", or the like may be used.

According to at least one embodiment described above, the motion information display apparatus and the program of the present embodiment can appropriately display a moving image of captured rehabilitation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A motion information display apparatus comprising:
processing circuitry configured to
obtain a first moving image of a first subject moving in a periodic manner, first motion information that indicates chronological change of a position of a characteristic point corresponding to a joint of the first subject in the first moving image, a second moving image of a second subject moving in a periodic manner, and second motion information that indicates chronological change of a position of a characteristic point corresponding to a joint of the second subject in the second moving image;
retrieve, from storage, definition information for defining a characteristic motion;
identify, by analyzing the first moving image based on the first motion information, a first frame corresponding to a timing when the first subject performed the characteristic motion corresponding to the definition information, from each frame group included in the first moving image;
identify, by analyzing the second moving image based on the second motion information, a second frame corresponding to a timing when the second subject performed the characteristic motion corresponding to the definition information from each frame group included in the second moving image;
cause play back of the first moving image and the second moving image to have respective timings of the play back that accord with each other, using the first frame and the second frame;
display a first graph showing the chronological change in the position of the characteristic point of the first subject, based on the first motion information;
display, on the first graph, a first marker showing a timing of motions corresponding to the first frame;
display a second graph showing the chronological change in the position of the characteristic point of the second subject, based on the second motion information; and
display, on the second graph, a second marker showing a timing of motions corresponding to the second frame.

2. The motion information display apparatus according to claim 1, wherein the processing circuitry is further configured to
obtain coordinates of the characteristic point in the first subject, as the first motion information,
obtain coordinates of the characteristic point in the second subject, as the second motion information,
identify the first frame based on the coordinates of the characteristic point in the first subject, and
identify the second frame based on the coordinates of the characteristic point in the second subject.

3. The motion information display apparatus according to claim 1, wherein
the processing circuitry is further configured to identify the first frame and the second frame, according to at least one of a type of rehabilitation and a purpose of rehabilitation.

4. The motion information display apparatus according to claim 1, wherein the processing circuitry is further configured to cause the play back of the first moving image and the second moving image to accord with each other by using parallel display or superimposition display to cause the timings of the playback to approximately accord with each other between the first moving image and the second moving image, using the first frame and the second frame.

5. The motion information display apparatus according to claim 1, wherein the processing circuitry is further configured to
identify a size of the subject included in each of the first and second motion information, and
cause the play back of the first moving image and the second moving image to accord with each other by causing the sizes of the first subject and the second subject to approximately accord with each other between the first and second moving images, using the sizes of the first subject and the second subject.

6. The motion information display apparatus according to claim 1, wherein the processing circuitry is further configured to cause the play back of the first moving image and the second moving image after translating and/or rotating at least one of the first moving image and the second moving image to cause directions of the first subject and the second subject to accord with each other between the first moving image and the second moving image.

7. The motion information display apparatus according to claim 1, wherein when causing the play back of the first moving image and the second moving image, the processing circuitry is further configured to display first skeleton information of the first subject included in the first moving image and second skeleton information of the second subject included in the second moving image.

8. A motion information display method comprising:
obtaining a first moving image of a first subject moving in a periodic manner, and first motion information that indicates chronological change of a position of a characteristic point corresponding to a joint of the first subject in the first moving image, a second moving image of a second subject moving in a periodic manner, and second motion information that indicates chronological change of a position of a characteristic point corresponding to a joint of the second subject in the second moving image;
retrieving, from storage, definition information for defining a characteristic motion;
identifying, by analyzing the first moving image based on the first motion information, a first frame corresponding to a timing when the first subject performed the characteristic motion corresponding to the definition information, from each frame group included in the first moving image;
identifying, by analyzing the second moving image based on the second motion information, a second frame corresponding to a timing when the second subject performed the characteristic motion corresponding to the definition information, from each frame group included in the second moving image;
causing play back of the first moving image and the second moving image to have respective timings of the play back that accord with each other, using the first frame and the second frame;
displaying a first graph showing the chronological change in the position of the characteristic point of the first subject, based on the first motion information;
displaying, on the first graph, a first marker showing a timing of motions corresponding to the first frame;
displaying a second graph showing the chronological change in the position of the characteristic point of the second subject, based on the second motion information; and
displaying, on the second graph, a second marker showing a timing of motions corresponding to the second frame.

9. The motion information display apparatus according to claim 1, wherein the first motion and the second motion are defined by at least one of positional relationship between a plurality of characteristic points of a human body and chronological change of position of a characteristic point of the human body.

* * * * *